United States Patent [19]
Sato et al.

[11] Patent Number: 6,127,681
[45] Date of Patent: Oct. 3, 2000

[54] SCANNING TUNNEL MICROSCOPE

[75] Inventors: Chiaki Sato, Kokubunji; Kiyozo Koshiishi; Sadao Shigetomi, both of Sagamihara; Shuzo Mishima; Tsugiko Takase, both of Hachiooji, all of Japan

[73] Assignee: Olympus Optical Co., Ltd., Tokyo, Japan

[21] Appl. No.: 07/460,076

[22] PCT Filed: Aug. 12, 1988

[86] PCT No.: PCT/JP88/00804

§ 371 Date: Feb. 5, 1990

§ 102(e) Date: Feb. 5, 1990

[87] PCT Pub. No.: WO89/01603

PCT Pub. Date: Feb. 23, 1989

[30] Foreign Application Priority Data

Aug. 12, 1987 [JP] Japan ................................. 62-201281

[51] Int. Cl.[7] .................................................. G12B 21/20
[52] U.S. Cl. .......................... 250/306; 250/307; 73/105
[58] Field of Search ............................. 250/306, 442.11, 250/307; 356/375, 376; 73/105

[56] References Cited

U.S. PATENT DOCUMENTS

| | | | |
|---|---|---|---|
| 4,343,993 | 8/1982 | Binning et al. | 250/306 |
| 4,732,485 | 3/1988 | Morita et al. | 356/376 |
| 4,785,177 | 11/1988 | Besocke | 250/306 |
| 4,894,538 | 1/1990 | Iwatsuki et al. | 250/306 |
| 4,914,293 | 4/1990 | Hayashi et al. | 250/306 |
| 4,921,346 | 5/1990 | Tokumoto et al. | 250/306 |
| 4,999,495 | 3/1991 | Miyata et al. | 250/306 |
| 5,260,824 | 11/1993 | Okada et al. | 359/368 |

FOREIGN PATENT DOCUMENTS

| | | |
|---|---|---|
| 0027517 | 4/1981 | European Pat. Off. . |
| 0 195 349 A2 | 9/1986 | European Pat. Off. . |
| 0 296 871 A2 | 12/1988 | European Pat. Off. . |
| 59-155508 | 10/1984 | Japan . |
| 63-111604 | 7/1988 | Japan . |

OTHER PUBLICATIONS

Journal of Vacuum Science & Technology, Part A, vol. 6, No. 2, Mar./Apr. 1988, pp. 383–385, Design of a Scanning Tunneling Microscope for Biological Applications.

IBM Technical Disclosure Bulletin, vol. 30, No. 5, Oct. 1987, pp. 369–370, Optically transparent tip for tunneling microscopy.

Y. Kobayashi et al., "Measurement of Ultra–Microfigure by STM", Extended Abstracts (The 34th Spring Meeting, 1987), The Japan Society of Applied Physics and Related Societies No. 2 (with English translation).

*Primary Examiner*—Jack Berman
*Attorney, Agent, or Firm*—Frishauf, Holtz, Goodman, Langer & Chick, P.C.

[57] ABSTRACT

A scanning tunnel microscope is arranged by a combination of an optical microscope and a tunnel scanning unit. The scanning tunnel unit includes a probe held to be spaced apart from a sample placed on a sample table by a predetermined interval in an axial direction, and an actuator for axially moving the sample table and the probe to a tunnel region and relatively and three-dimensionally driving the sample table and the probe. An objective lens and the probe are arranged such that the axis of the probe of the scanning tunnel unit is aligned with an optical axis of the objective lens of the optical microscope. The sample and the probe are axially moved and brought into the tunnel region, and the sample is scanned in its surface direction while the sample and the probe are finely moved in the axial direction and a tunnel current is kept constant, thereby performing an STM observation of an observation surface of the sample. The objective lens of the optical microscope is axially moved to obtain an in-focus state, and the field of the STM observation surface is observed as an optical microscopic image through an eyepiece lens.

199 Claims, 20 Drawing Sheets

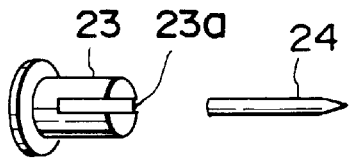
F I G. 3
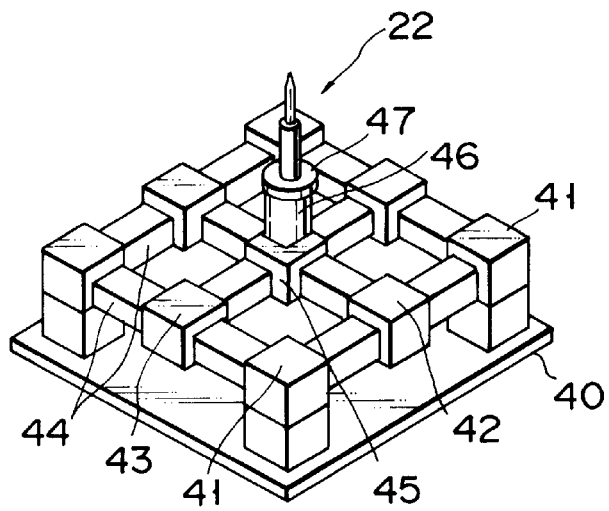
F I G. 4
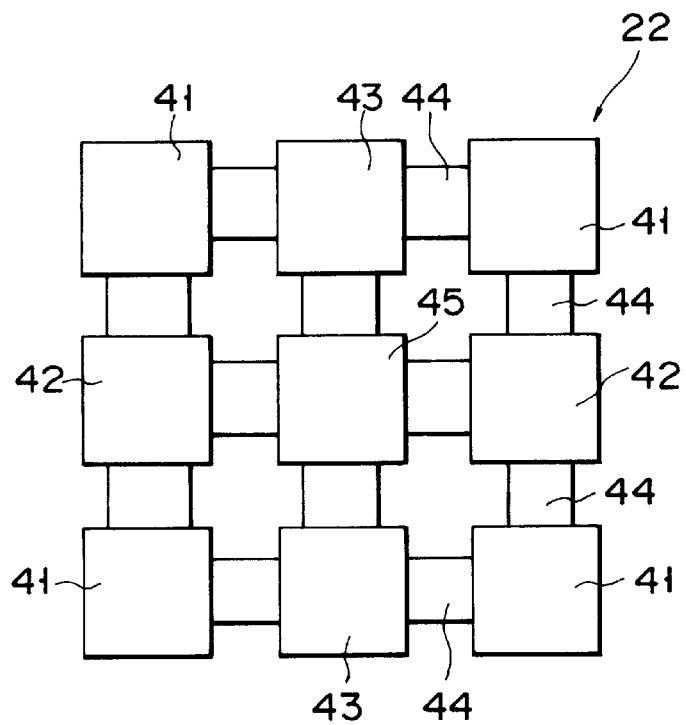
F I G. 5

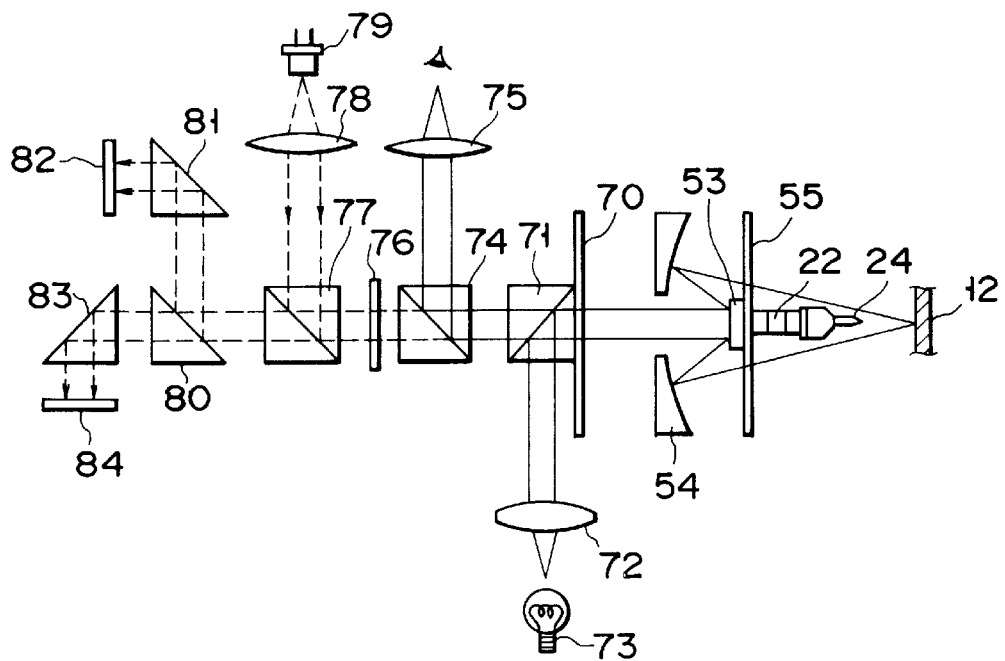
F I G. 8
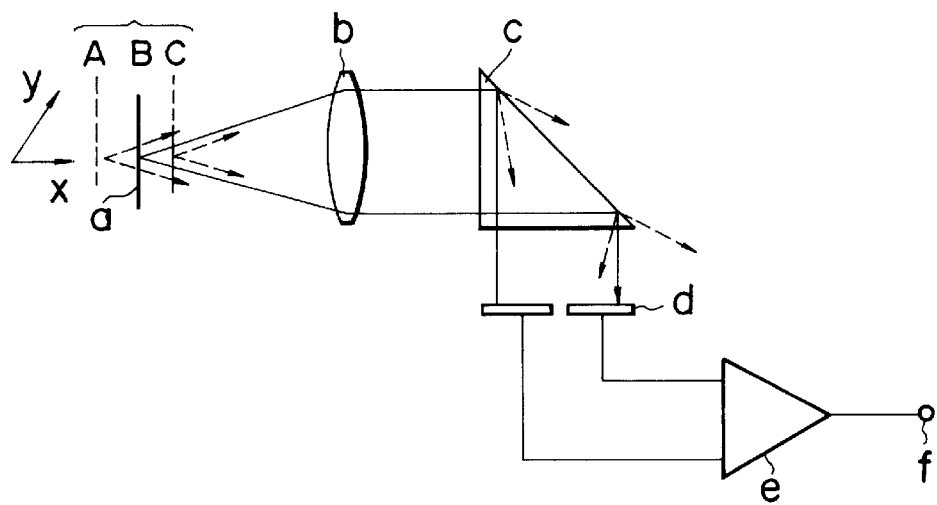
F I G. 9

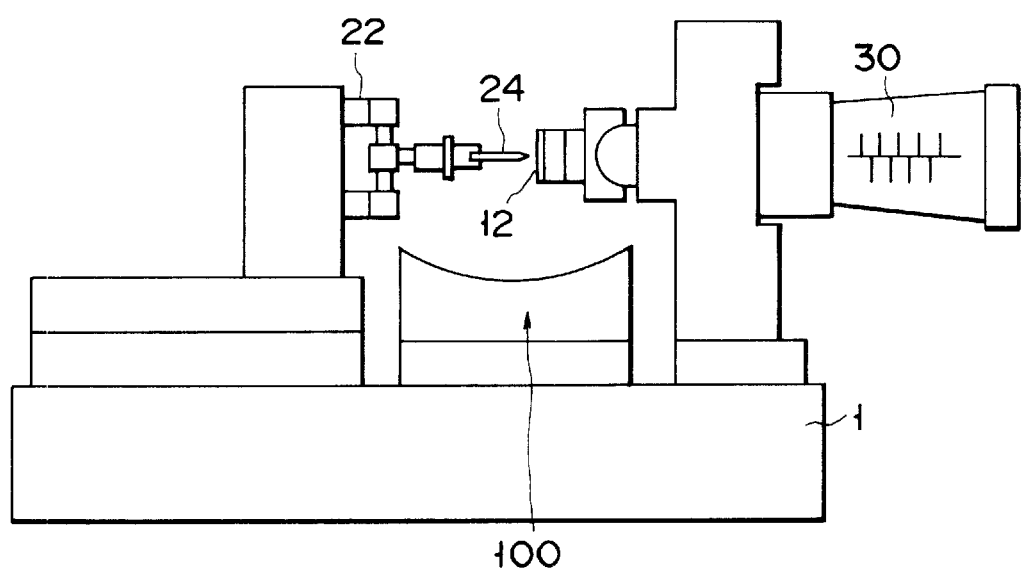
F I G. 10

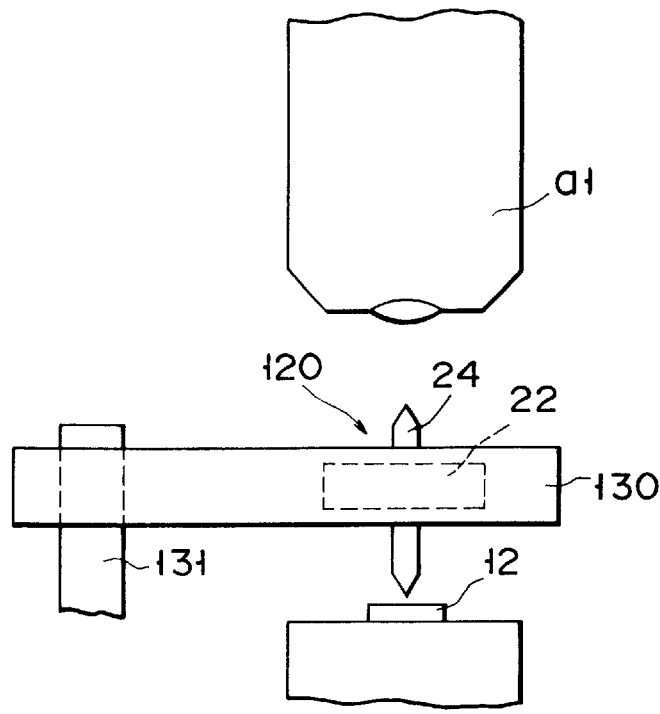
F I G. 14
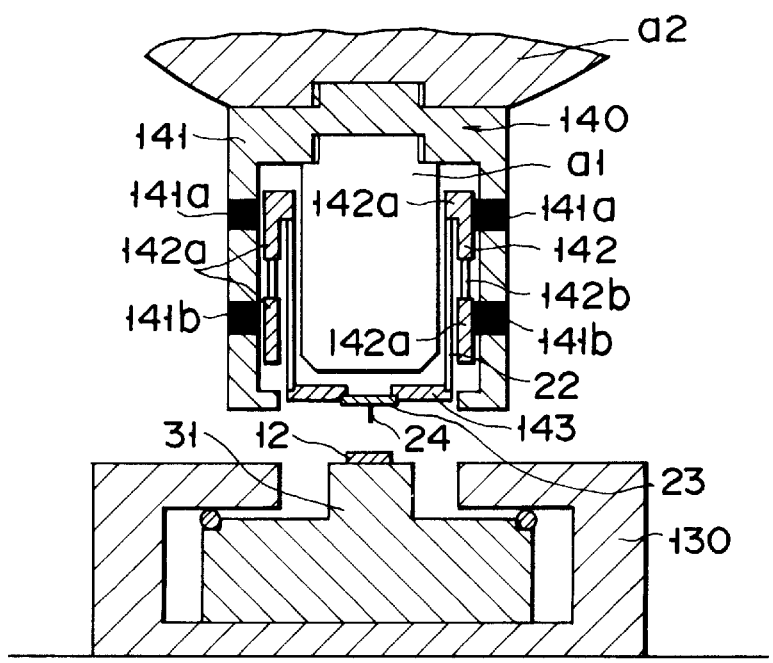
F I G. 15

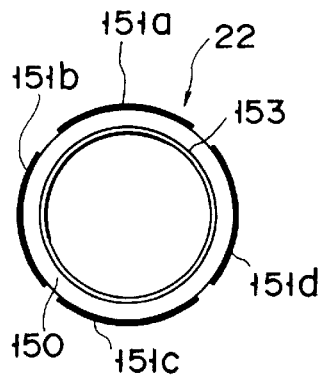
FIG. 16A
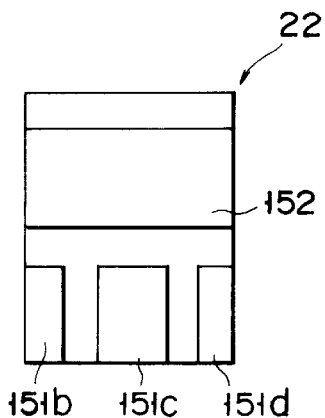
FIG. 16B
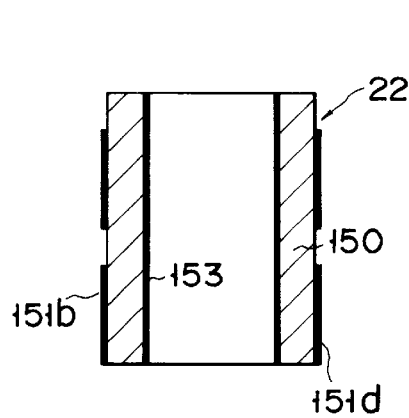
FIG. 16C
| ELECTRODE | APPLIED VOLTAGE | MOVING DIRECTION | APPLIED VOLTAGE | MOVING DIRECTION |
|---|---|---|---|---|
| X | + | +x | − | −x |
| Y | + | +y | − | −y |
| $\overline{X}$ | − | +x | + | −x |
| $\overline{Y}$ | − | +y | + | −y |
| Z | + | +z | − | −z |
FIG. 16D

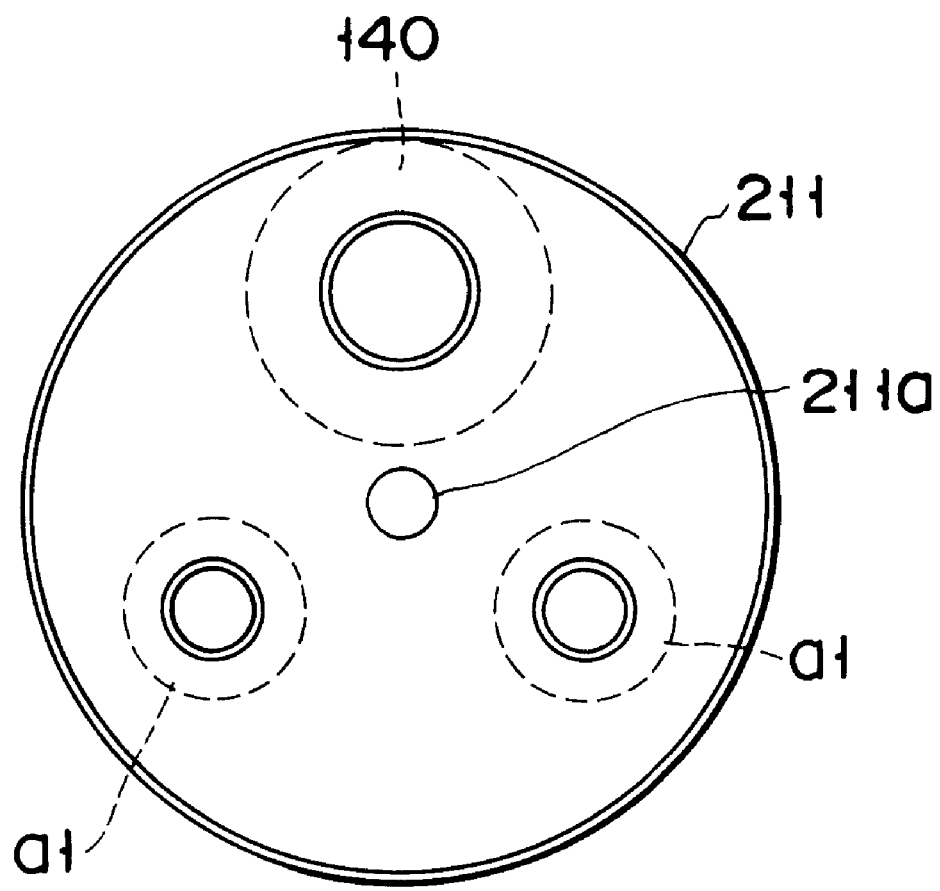
F I G. 21C

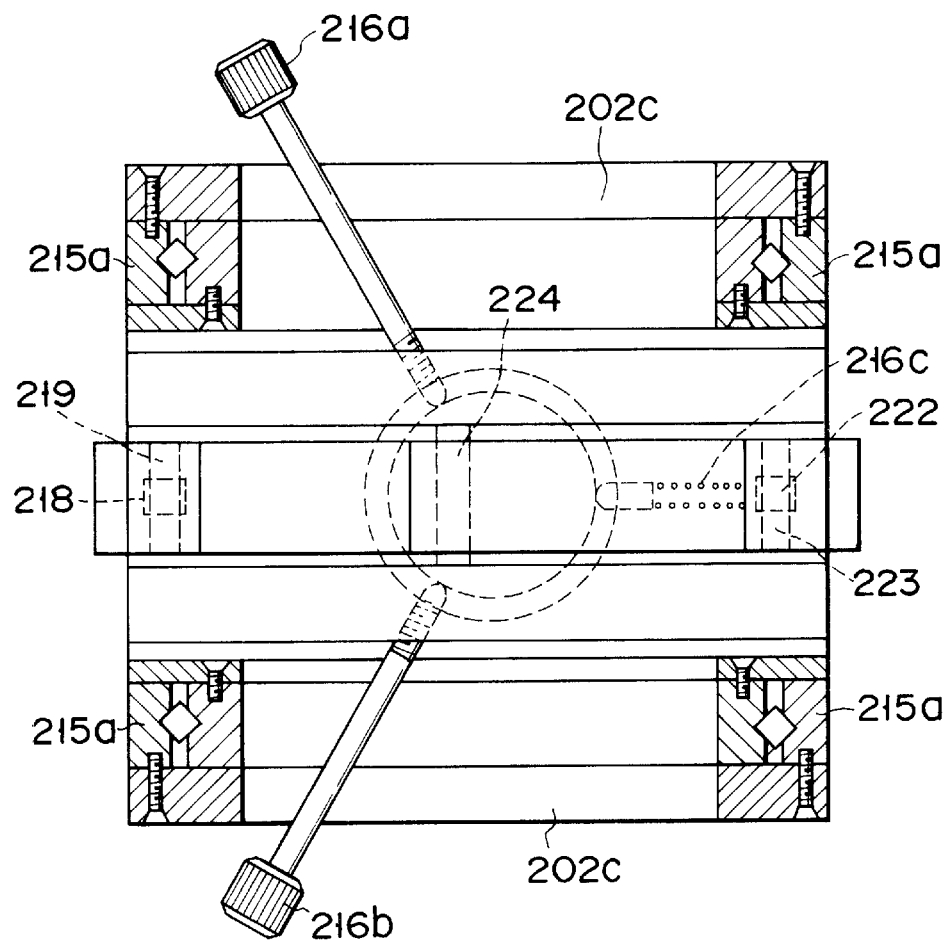
F I G. 21D

SCANNING TUNNEL MICROSCOPE

TECHNICAL FIELD

The present invention relates to a scanning tunnel microscope (STM) for causing a metal probe to come close to an observation surface of a sample as much as possible, e.g., 50 Å or less to detect and measure a tunnel current flowing between the metal probe and the sample, and imaging the tunnel current.

BACKGROUND ART

Unlike a conventional microscope, the STM can detect electrons constrained in a sample. In recent years, the STM has received a great deal of attention as a typical surface observation apparatus capable of observing atomic alignment in a real space. The principle of operation of such an STM will be described below.

A probe having a sharp tip comes close to a sample surface by an z-direction actuator such that electron clouds smeared out from the sample surface slightly overlap each other, and a voltage (tunnel voltage) is applied between the probe and the sample to cause a tunnel current to flow from the probe to the sample. The z-direction actuator is servo-controlled to keep this tunnel current constant. At the same time, the probe and the sample are relatively moved in a surface direction by an xy-direction actuator to perform two-dimensional scanning. At this time, a servo voltage applied to the z-direction actuator which servo-controls the probe is read, and the read voltage is displayed as an image, thereby observing the surface of the sample. That is, the probe scans the sample surface. When a scanning position reaches a step on the sample surface, a tunnel current is increased. The probe is separated from the sample by the z-direction actuator until the tunnel current reaches a constant value (initial value). Since this probe movement corresponds to the step on the surface, this scanning operation is repeated to read servo voltages, thereby obtaining a surface image of the sample.

The tunnel current $J_T$ is represented by the following relation:

$$JT \exp(-A \cdot \phi^{1/2} \cdot S)$$

where

A: a constant $\phi$: an average of work functions of the probe and the sample

S: a distance between the probe and the sample

The tunnel current JT therefore changes in accordance with a change in distance S with high response, and a resolution of an atomic scale can be obtained.

As described above, the STM can obtain a surface image of a substance with a high resolution. Unlike a reciprocal lattice space image obtained by a method such as electron beam diffraction or ion scattering, the STM has a characteristic feature capable of observing atomic alignment in a real space. In addition, a voltage applied between the probe and the sample has a value smaller than the work function of the sample. Since the tunnel current is detected on the nA order, power consumption is low, and the damage to the sample is little.

Although a conventional STM can obtain a surface image having a very high resolution in the real space, an observation portion is unclear or the STM is not suitable for observation for a specific portion within a narrow range because the observation portion on the sample surface is observed with eyes and the above observation operation is performed. In addition, an STM image can't be compared with a conventional image obtained by other microscopes (e.g., an optical microscope and an electron microscope), and an STM observation region (STM field) does not necessarily coincide with the conventional observation field.

The present invention therefore has been made in consideration of problems of the above prior art, and has as its object to provide a scanning tunnel microscope capable of allowing an STM image to overlap a conventional image and observing and measuring the STM image.

DISCLOSURE OF INVENTION

A scanning tunnel microscope according to the present invention is characterized by comprising a sample table for holding a sample, a probe held to be spaced apart from the sample by a predetermined interval in an axial direction, an actuator for axially moving the sample table and the probe to allow them to come close to a tunnel region and three-dimensionally driving the sample table and the probe relative to each other, fixing means for fixing the actuator, and an optical microscope held in the fixing means and having an optical objective member axially movable with respect to a surface of the sample and an optical eyepiece member for receiving light reflected from the sample through the optical objective member, the optical microscope being able to observe a surface of the sample through the optical eyepiece member.

In the scanning tunnel microscope having the above arrangement, the sample and the probe are axially moved by the actuator and are brought into the tunnel region. The sample and the probe are finely moved to Scan the sample in a surface direction while a tunnel current is kept constant, thereby achieving an STM observation of the observation surface of the sample. The optical objective member of the optical microscope is axially moved to perform focusing on the observation surface, and the field of the STM observation surface can be measured through the optical eyepiece member.

BRIEF DESCRIPTION OF THE DRAWINGS

FIGS. 1 to 5 show a scanning tunnel microscope according to an embodiment of the present invention, in which FIG. 1 is a plan view showing the overall structure thereof, FIG. 2 is a side view thereof, FIG. 3 is a perspective view showing a probe and its holder, FIG. 4 is a perspective view of a three-dimensional actuator, and FIG. 5 is a plan view of this three-dimensional actuator.

FIG. 8 is a schematic view showing a modification obtained by adding a geometric measurement function to the apparatus of the second embodiment.

FIG. 9 is a view for explaining the principle of geometric measurement.

FIG. 10 is a side view showing a modification obtained by adding a monitor unit to the apparatus of the first embodiment.

FIG. 14 is a sectional view showing the fifth embodiment.

FIG. 15 is a sectional view showing an objective lens unit showing the sixth embodiment.

FIGS. 16A through 16C show a three-dimensional actuator used in the embodiment, in which FIG. 16A is a plan view thereof, FIG. 16B is a side view thereof, and FIG. 16C is a sectional view thereof.

FIG. 16D is a view showing a relationship between a voltage applied to drive the three-dimensional actuator and a drive direction of the actuator.

FIGS. 19A to 19C show a scanning tunnel microscope of the ninth embodiment, in which FIG. 19A shows a state wherein a tunnel scanning unit is not located at an STM scanning position, FIG. 19B shows a state wherein the tunnel scanning unit is located at the STM scanning position, and FIG. 19C is a view showing a state wherein the tunnel scanning unit is combined with an optical microscope.

FIGS. 21A to 21D show a measurement unit shown in the tenth embodiment, in which FIG. 21A is a cross-sectional view, FIG. 21B is a longitudinal sectional view, FIG. 21C is a view showing a positional relationship between an objective revolver, an objective lens, and an objective lens unit, and FIG. 21D is a sectional view taken along the horizontal direction.

FIGS. 24A to 24C show a modification of the measurement unit, in which FIG. 24A is a partially cutaway plan view, FIG. 24B is a sectional view, and FIG. 24C is a side view showing part of an interval measurement unit.

(F) EMBODIMENTS

Figure 1:
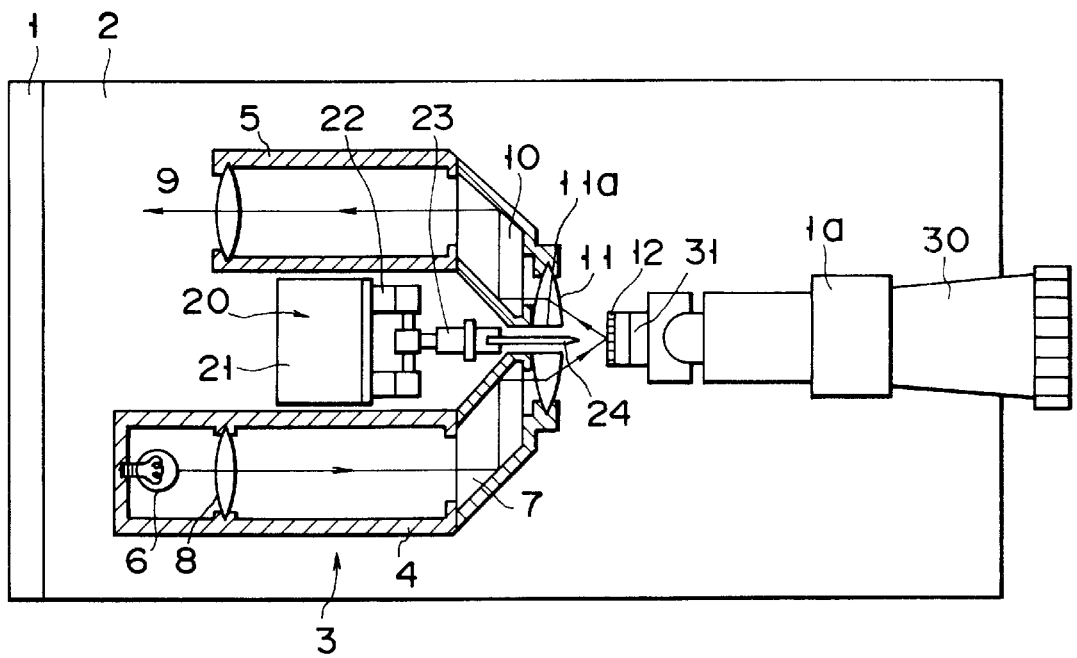

Scanning tunnel microscopes according to embodiments of the present invention will be described with reference to the accompanying drawings. The same reference numerals denote the same members having substantially the same functions throughout the embodiments to be described below.

Figure 2:
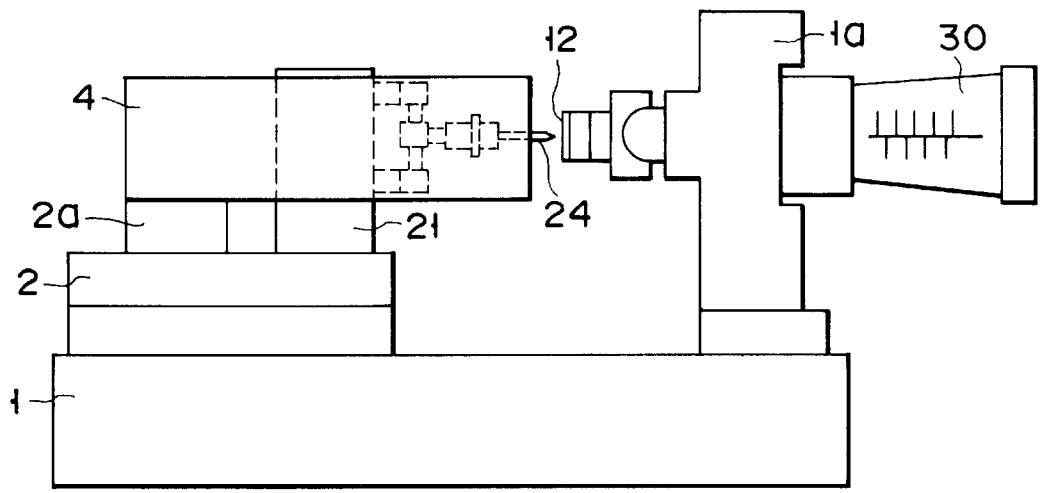

In FIGS. 1 and 2 which show the first embodiment, reference numeral 1 denotes a base. A movable stage 2 is mounted on the base 1 so as to be movable in the z direction. An STM field observation optical system (optical microscope) 3 is fixed on the movable stage 2 by a column 2a. This system 3 has a cylindrical light source housing 4 and a cylindrical observation housing 5 in tandem with the housing 4. A light source 6, a first prism 7, and a focusing lens 8 are arranged at one end, near the other end, and at a middle portion in the light source housing 4, respectively. A focusing lens 9 and a second prism 10 are arranged at one end and near the other end in the observation housing 5, respectively. A common convergent lens 11 (objective lens) is mounted at the other-end portions of the housings 4 and 5. A through hole 11a is formed at the center of the convergent lens 11.

In the STM field observation optical system having the above arrangement, light emitted from the light source 6 is focused and collimated by the focusing lens 8, and the collimated beam is incident on the first prism 7. The incident beam is reflected twice at a right angle and passes part of the convergent lens 11. As a result, the beam is focused on an observation surface of a sample 12 located on the front surface of the convergent lens 11. A beam reflected by the sample 12 passes through the other part of the convergent lens 11 and is incident on the observation housing 5. The optical path of the beam is changed by the second prism 11 and is focused by the focusing lens 9. Therefore, an observer can observe the observation surface of the sample through the focusing lens 9. When focusing is performed in this system, the movable stage 2 is moved in the z direction to move the convergent lens 11 toward the sample or away from it. Of course, the sample 12 may be moved toward the convergent lens 11 or away from it in the z direction. A moving unit for the sample 12 will be described later.

Reference numeral 20 in FIG. 1 denotes an STM system. This system 20 has an actuator mounting table 21 fixed on the movable stage 2. A three-dimensional actuator 22 finely movable in the x, y, and z directions is fixed on the mounting table 21. A probe holder 23 extends at the central portion of this actuator. The probe 24 is detachably mounted at the proximal end of this holder. The distal end of the probe 24 extends through the through hole 11a formed at the center of the convergent lens 11 and extends toward the sample 12. The outer diameter of the probe 24 is determined such that the probe 24 is movable in the through hole 11a in the axial direction (the z direction). A split portion 23a is formed on the front end face of the probe holder 23, as shown in FIG. 3. The probe 24 is detachably held in the split portion 23a by inserting the proximal portion of the probe 24 into the split portion 23a under pressure. The sample 12 is held on a sample table 31 formed at the distal end of a coarse moving unit 30 so as to oppose the convergent lens 11. The coarse moving unit 30 comprises, e.g., a differential micrometer which is fixed on the base 1 by a block 1a and can perform coarse movement of the sample table 31 in the x direction.

The three-dimensional actuator 22 will be described with reference to FIGS. 4 and 5.

Referring to FIGS. 4 and 5, reference numeral 40 denotes a stand, one surface of which is mounted on the actuator mounting table 21 fixed on the base 1 and which comprises an electrically insulating plate. Four common electrodes 41 located at four corners of a square are fixed on the other surface of the stand 40, and x and an electrodes 42 and 44 are connected between the common electrodes 41 through piezoelectric elements 44. A central electrode 45 is located at the center of the table 40 such that the central electrode 45 is connected to the x and y electrodes 42 and 43 through other piezoelectric elements 44. A piezoelectric element 46 extendible in the z direction is fixed on the central electrode 45. The probe holder 23 is fixed at the distal end face of the piezoelectric element 46 through an insulating plate 47. These electrodes and the piezoelectric elements comprise cubic members, respectively. Each electrode is slightly larger than each piezoelectric element, as shown in FIGS. 4 and 5. The polarity of the right piezoelectric elements 44 is opposite to that of the left piezoelectric elements 46 with respect to the central electrode 45. For example, when a predetermined voltage is applied to the electrodes, the right piezoelectric elements 44 with respect to the central electrode 45 contract, while the left piezoelectric elements 46 with respect to the central electrode 45 extend. When the central electrode 45 is grounded and a voltage of Vx>0 is applied to the x electrodes 42, the central electrode 45 is moved to the right. However, when a voltage of Vx<0 is applied to the x electrodes 42, the central electrode 45 is moved to the left. As a result, when an AC voltage is applied to the x electrodes, the probe mounted on the central electrode 45 can be vibrated in the x direction. Similarly, when the Vy AC voltage is applied to the y electrodes, the probe can be vibrated in the y direction. In this case, in order to vibrate the probe simultaneously in the x and y directions, an AC voltage of Vx+Vy must be applied to the electrodes located at the four corners. By using the above AC voltages, the probe is moved in the xy direction to scan the observation surface of the sample 12. A servo operation for keeping a tunnel current constant is performed such that a servo signal is input from a control unit to extendible piezoelectric elements 46 in the z direction to keep the distance between the probe and the observation surface of the sample constant.

In the STM system 20 having the above arrangement, the movable stage 2 is coarsely moved in the z direction to cause the probe 24 to come closer to the sample 12 than the focusing position of the optical system 3. The coarse moving unit 30 is finely controlled until a tunnel current can be detected, i.e., until the probe 24 and the sample 12 enter a tunnel region. In this state, the probe 22 is finely moved in the x-y direction (surface direction) and the z direction (axial direction) while the tunnel current is kept constant, thereby scanning the observation surface of the sample 12.

A scanning tunnel microscope according to the second embodiment of the present invention will be described with reference to FIGS. 6 and 7.

In this embodiment, a mechanism for holding a sample 12 and a coarse movement driving mechanism for an STM field observation optical system 3 and a probe 24 are the same as those of the above embodiment, and a detailed description thereof will be omitted.

The optical system 3 has a light source 50 and a focusing lens 51 for focusing light from the light source 50. A splitting prism 52 for splitting the incident light into a transmitted beam and a 90° reflected beam is arranged in front of the focusing lens 51. A convex mirror 53 for diffusing and reflecting the incident beam and a concave mirror 54 for reflecting a beam reflected by the convex mirror and focusing it on the observation surface of the sample 12 are arranged on the transmitted beam side of the prism 53. The convex mirror 53 is fixed at the central portion of the rear surface of a transparent support plate 55. Note that the beam reflected by the concave mirror 54 is transmitted through a peripheral portion of the support plate 55 and is incident on the sample 12. The three-dimensional actuator 22 is fixed on the front surface of the support plate 55. The probe 24 is supported at the distal end of this actuator through an insulating plate 47 and a probe holder 23. A focusing lens 56 is arranged on the reflection side of the splitting prism 52. An observer can observe a microscopic image from an observation surface of the sample 12 by a beam reflected by the sample 12 through the concave mirror 54, the convex mirror 53, and the prism 52.

The three-dimensional actuator 22 used in the apparatus of the second embodiment can have the same structure as in the first embodiment. However, an actuator having a structure different from that of the first embodiment is used in the second embodiment and will be described with reference to FIG. 7.

This actuator 22 has three piezoelectric elements 60, 61, and 62. A voltage application direction of the first piezoelectric element 60 is the same as its polarization direction. The first piezoelectric element 60 extends or contracts by electrodes 63 and 64 arranged at both ends thereof in directions of arrows (z direction). When a voltage is applied to the second and third piezoelectric elements 61 and 62 in a direction perpendicular to their polarization direction, a shearing force acts on the elements 61 and 62, and a slip force is generated in the polarization direction. In this manner, the second and third piezoelectric elements 61 and 62 are arranged such that their polarization directions are perpendicular to each other. Electrodes 65 and 66 are formed between the second piezoelectric element 61 and the third piezoelectric element 62 and between the third piezoelectric element 62 and the insulating plate 47, respectively. When a voltage is applied between the electrodes 64 and 65, the second piezoelectric element 61 can extend or contract in the y direction. When a voltage is applied between the electrodes 65 and 66, the third piezoelectric element 62 can extend or contract in the x direction.

The same scanning as in the first embodiment is performed n the apparatus of the second embodiment to allow an STM observation of the sample 12. At the same time, the STM field can be observed with an optical microscope. Note that when the optical field observation optical system is constituted by a reflecting objective lens system as in this embodiment, a W.D can be increased as compared with an arrangement obtained by a refracting objective lens system. Contact between the probe and the sample and hence damage to the probe can be prevented, and at the same time an optical field can be observed. This optical system has advantages in that there is no chromatic aberration and the focal position does not have wavelength dependency. Therefore, focal control of invisible light can be facilitated.

An arrangement obtained by adding a function of optically measuring a geometry of the observation surface of the sample to the optical system of the apparatus of the second embodiment will be described with reference to FIG. 8.

Referring to FIG. 8, reference numeral 70 denotes another transparent support plate fixed so that its front surface opposes the transparent support plate 55. A first splitting prism 71 is fixed on the rear surface of the support plate 70. A light source 73 is arranged at a lateral position from the prism 71 through a focusing lens 72. Light emitted from the light source 73 is focused by the focusing lens 72 and is incident on the first splitting prinosm 71. The light is then reflected through 90° and is incident on the sample 12 through the convex mirror 53 and the concave mirror 54. A beam reflected by the sample 12 is incident on the first splitting prism 71. A second splitting prism 74 is located on the transmission side of the splitting prism 71, and an eyepiece lens 75 is located on the opposite side of the prism 74. The reflected beam incident on the first splitting prism 71 is partially reflected by the second splitting prism and is guided to the eyepiece lens 75. As a result, the observer can microscopically observe the observation surface of the sample 12 through the eyepiece lens 75 in the same manner as in the second embodiment.

The geometric measurement unit arranged on the transmission side of the second splitting prism 74 will be described below. This unit includes a third splitting prism 77 arranged on the transmission side of the second splitting prism 74 through a λ/4 plate 76. A laser diode 79 is arranged at a lateral position from the third splitting prism 77 through a focusing lens 78. A fourth splitting prism 80 constituting a polarized beam splatter is arranged at a lateral position from the third splitting prism 77. A first photodiode 82 is located on the opposite side of the fourth splitting prism 80 through a first critical angle prism 81. A second photodiode 84 is located on the transmission side of the fourth splitting prism 80 through a second critical angle prism 83.

An operation of the geometric measurement unit having the above arrangement will be described below.

A beam emitted from the laser diode 79 is collimated by the focusing lens 78. The collimated beam is incident on the third splitting prism 77 and is reflected by this prism through 90°. The reflected beam passes through the λ/4 plate 76 and is incident on the sample 12 through the second splitting prism 74, the first splitting prism 71, the convex mirror 53, and the concave mirror 54, thereby forming a very small spot on the observation surface. A beam reflected by the observation surface passes through an optical path opposite to the incident beam, is reflected by the λ/4 plate 76, and then passes through the third splitting 77. This beam is p-polarized by the third splitting prism 77 and is then incident On the fourth splitting prism 80 and split into two beams. One beam is incident on the first photodiode 82 through the first critical angle prism 81, and the other beam is incident on the second photodiode 84 through the second critical angle prism 83. In this apparatus, the beams respectively incident on the first and second critical angle prisms 81 and 83 have different incident angles due to projections on the observation surface of the sample 12, and beams incident at angles exceeding the critical angle emerge outside the prisms 81 and 83. Detection light amounts of the photodiodes 82 and 84 are changed, thereby optically obtaining projection information of the observation surface of the sample 12.

The principle of the optical geometric measurement apparatus will be briefly described with reference to FIG. 9.

When an observation surface (measurement surface) a of the sample is located at the focal position of an objective lens b (corresponding to the convex and concave mirrors), a reflected beam having passed through the objective lens b is collimated, and the collimated beam is incident on a critical angle prism At this time, an optical system is set such that an angle formed by an incident beam and a reflecting surface of the prism c is set to be a critical angle. However, when the observation surface a is located at a position on the objective lens a side (a position indicated by a dotted line A), a beam reflected by the observation surface a is diverged by the objective lens b. On the other hand, when the observation surface a is located at a position far from the focal position (a position indicated by a dotted line C), a convergent beam is obtained. In these cases, only the central beam is incident on the critical angle prism c. Beams deviated toward one side from the center have incident angles smaller than the critical angle, and some beams are refracted and emerge outside the prism c. In this case, the remaining beams are reflected. Beams located on the other side have incident angles larger than the critical angle and are totally reflected. By the above operations, an amount of light incident on the right photodiode of the two-split photodiodes d is different from that on left photodiode. As a result, a differential signal appears at an output terminal f through an operational amplifier e, the input terminals of which are connected to the photodiodes, respectively. Therefore, the focal position of the objective lens b is optically detected to obtain projection information of the observation surface. A predetermined area of the observation surface in the xy direction is scanned, and a three-dimensional image of the observation surface can be obtained.

In the embodiment shown in FIGS. 8 and 9, a measurement of a very small displacement of the surface of the sample, i.e., a critical angle method as an example of a displacement measurement optical system has been described above. However, the displacement measurement optical system is not limited to the critical angle method, but a known optical system utilizing a focal detection system can be used (see U.S. Pat. Nos. 4,726,685 and 4,732,485). For example, an optical system utilizing astigmatism can be used.

A scanning tunnel microscope shown in FIG. 10 is obtained by adding a monitor unit 100 consisting of a concave mirror to an arrangement of FIG. 2 to facilitate relative movement between the probe 24 and the sample 12. The concave mirror is fixed on the base 1 so as to be located at an intermediate position between the three-dimensional actuator 22 and the coarse moving unit 30. The concave surface is directed upward so that the probe 24 and the sample 12 are located within the focal point of the concave mirror. An enlarged erecting virtual image is observed through the concave mirror, thereby detecting a distance between the probe 24 and the sample 12.

In the apparatus of each embodiment described above, in optical microscopic observation, polarization of an observation magnification can be performed by an eyepiece lens. However, this may be achieved by employing a revolver type objective lens arrangement.

Figure 6:
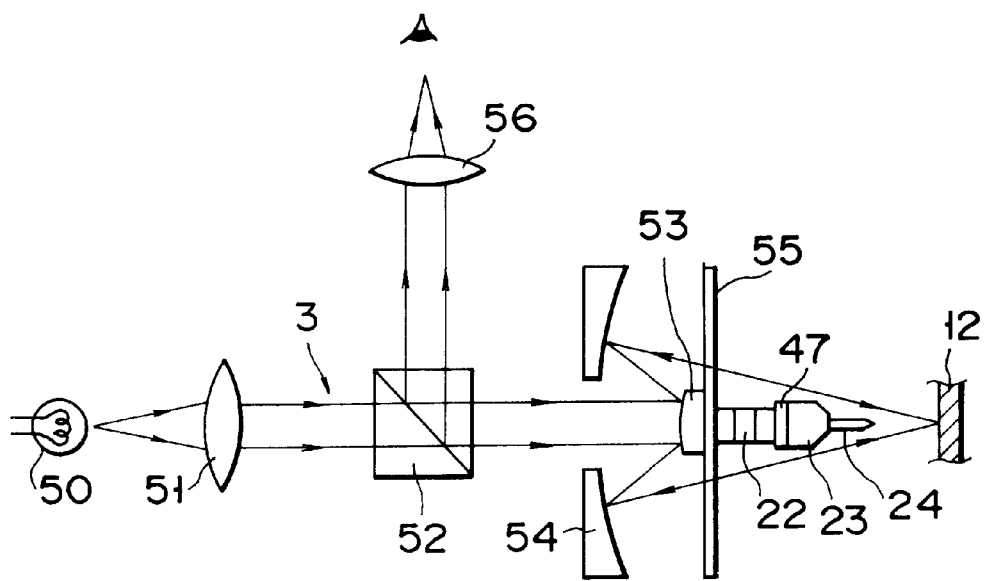
FIG. 6 is a schematic view showing a scanning tunnel microscope according to the second embodiment of the present invention.
Figure 7:
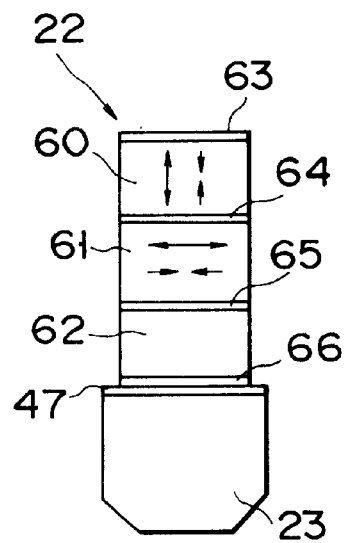
FIG. 7 is a side view showing a three-dimensional actuator used in the second embodiment.

When the optical system field observation optical system is constituted by a reflection objective lens system as in the embodiment shown in FIGS. 6 and 8, an interval between the fixed concave mirror 54 and the convex mirror 53 moved together with the probe 24 may be deviated from the accurate interval upon contact between the probe 24 and the sample 12, and the optical microscopic image may be degraded. In this case, the convex mirror 53 and the concave mirror 54 may be formed integrally, and its example will be described below.

Figure 11:
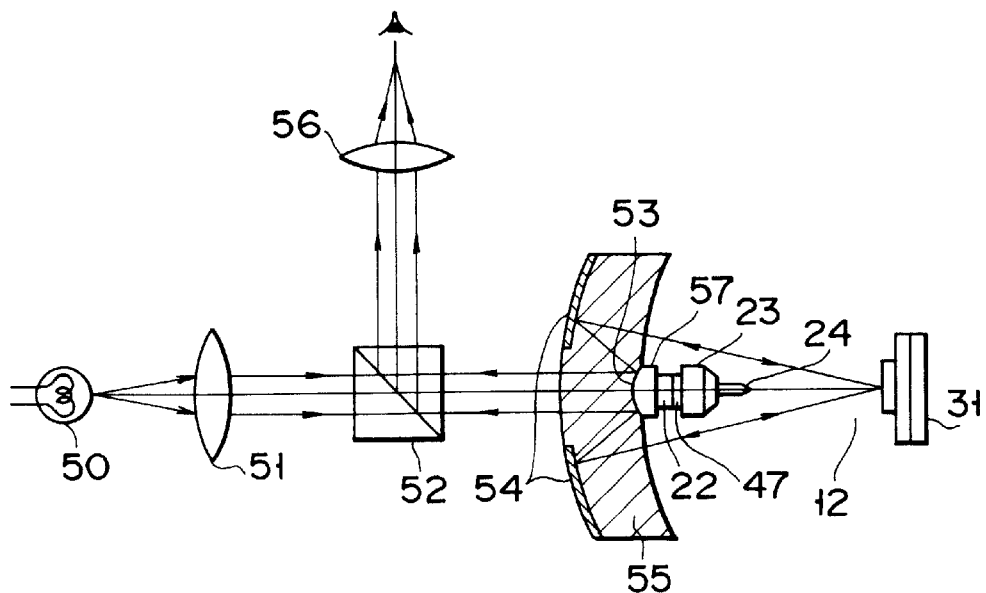
FIG. 11 is a view showing a modification of the embodiment shown in FIG. 6.

FIG. 11 shows a modification of only the lens system in the apparatus shown in FIG. 6 in accordance with the above concept. Referring to FIG. 11, reference numeral 55 denotes a transparent quartz plate whose front and rear surfaces have predetermined curvatures. A deposition film having a high reflectance is formed on the rear surface except for the central portion, thereby constituting a concave mirror 54. A circular recess is formed at the central portion of the front surface of the quartz plate 55. A transparent quartz support 56 whose convex mirror 53 is formed on its rear surface in the same manner as the concave mirror 54 is inserted and fixed in this recess. The three-dimensional actuator 22 for driving the probe 24 is fixed on the front surface of this support. As a result, since the convex mirror 53 and the concave mirror 54 are formed integrally with the quartz plate 55, the interval therebetween is not changed even if the probe 24 is brought into contact with the sample 12. With this arrangement, the radius of curvature of the convex mirror 53 is set to be smaller than that of the concave mirror 54, and the curvature of a front surface portion of the quartz plate 55 which does not have the support 56 is set to be equal to that of the convex mirror 53.

In the above modification, a light-shielding plate for shielding illumination light may be inserted between the focusing lens 51 and the splitting prism 52 during STM observation. The actuator 22 may be constituted by a one-dimensional actuator for driving the probe 24 in only the z direction, and the sample table 31 may be constituted by a two-dimensional actuator movable in the x and y directions.

In each embodiment described above, since the STM field observation optical system and the STM observation system are combined integrally, it is not suitable to apply the technique of the present invention to a general-purpose optical microscope without any modifications. For this reason, an embodiment of a scanning tunnel microscope which can employ a general-purpose microscope without almost any modifications will be described below.

Figure 12:
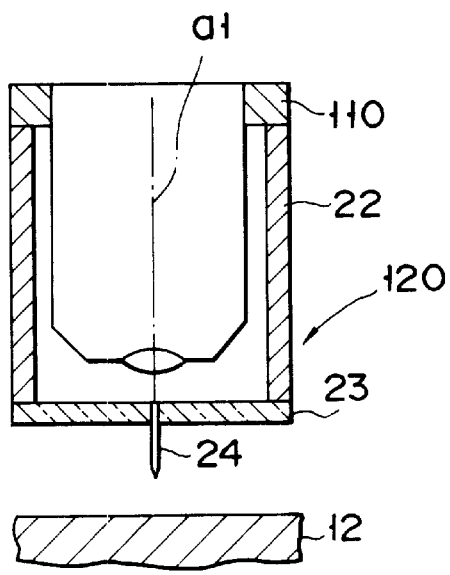
FIG. 12 is a sectional view of an objective lens unit showing the third embodiment.

In FIG. 12 showing a scanning tunnel microscope of the third embodiment, reference numeral 110 denotes an annular support member for supporting a cylindrical three-dimensional actuator 22 on an objective lens a1 of a general-purpose microscope. The support member 110 is detachable from the outer circumferential surface of the objective lens a1 and coaxial with the objective lens a1. The support member 110 and the objective lens al are connected by, e.g., threadable engagement or bolting. The upper end of the three-dimensional actuator 22 is fixed or detachably mounted on the support member 110. A transparent plate, e.g., a probe holder 23 made of cover glass is coaxially mounted on the lower end of the actuator 22. A through hole is formed in the center of the holder 23. The proximal end of the probe 24 is inserted into this through hole, and the probe 24 is fixed in the holder 23 by, e.g., an adhesive. The probe 24 is connected coaxially with the holder 23 with high precision. In addition, the axes of the probe 24 and the holder 23 coincide with the optical axis of the objective lens a1. As described above, the support member 110, the actuator 22, the probe holder 23, and the probe 24 constitute a tunnel scanning unit 120. In the scanning tunnel microscope having the above arrangement, an STM scanning area of the observation surface of the sample 12 is microscopically observed through the transparent holder 23 while the tunnel scanning unit 120 is mounted on the objective lens a1 such that the axis of the probe 24 coincides with the optical axis of the objective lens a1. In the same manner as in the previous embodiment, the probe 24 is three-dimensionally moved by the actuator 22 to observe the STM area. In this manner, in the apparatus of this embodiment, the STM image can be observed and measured while it overlaps the conventional image as in the apparatus of the previous embodiments.

Figure 13:
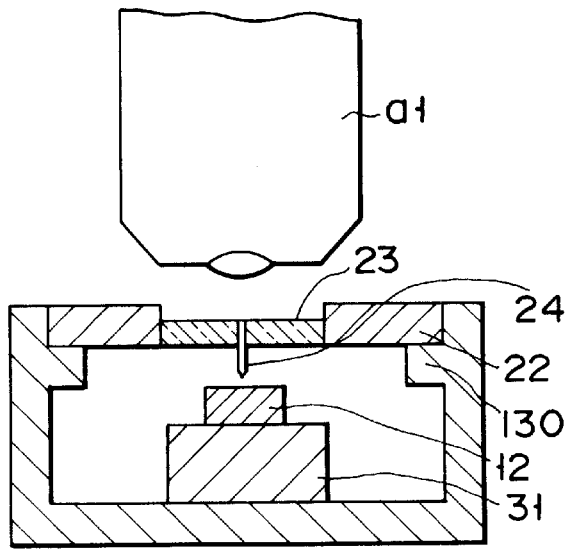
FIG. 13 is a sectional view of a tunnel scanning unit showing the fourth embodiment.

In the fourth embodiment shown in FIG. 13, a three-dimensional actuator 22 is not mounted on an objective lens a1 but supported by a frame-like support member 130 which supports a sample table 31 therein. The support member 130 has a circular opening at the central portion of the upper wall. A ring-like actuator 22 is fixed on the peripheral surface of the opening so that the actuator 22 is coaxial with the objective lens a1. A probe holder 23 made of a transparent glass plate is mounted to seal the hole of the inner circumferential surface of the actuator 22. A probe 24 is mounted at the center of the holder 23 such that the probe 24 extends toward a sample 12 along the optical axis of the objective lens a1. In the fifth embodiment shown in FIG. 14, a support member 130 is supported by a support shaft 131 extending to be parallel to the optical axis of an objective lens a1 and is pivotal about the support shaft 131 on a horizontal plane. As a result, a tunnel scanning unit 120 consisting of a three-dimensional actuator 22 arranged at a free end of the support member 130, a transparent probe holder (not shown), and a probe 24 can be retracted from a path between the objective lens a1 and the sample 12. With this arrangement, the objective lens a1 is caused to come close to the sample 12 during observation of the conventional image. In the embodiment shown in FIG. 14, the transparent probe holder is used. However, any member other than the transparent holder may be used within the range which does not interfere the optical field, if the position of the probe can be specified. For example, a structure in which a probe is supported by a wire may be used.

In the sixth embodiment shown in FIG. 15, reference numeral 140 denotes an objective lens unit detachably mounted on a revolver a2 of a known optical microscope, e.g., a metallurgical microscope. The unit 140 comprises a cylindrical outer frame 141 having a projection on its outer surface and a lower open end. The projection has a male thread which is threadably engaged with a female thread of an objective lens of the revolver a2. A screw hole is formed at the center of the inner surface of the upper wall of the outer frame 141. The upper end of the objective lens a1 is threadably engaged with this screw hole. A cylindrical inner frame 142 is formed between the outer circumferential surface of the objective lens a1 and the inner circumferential surface of the outer frame 141. The inner frame 142 comprises a pair of support portions 142a vertically spaced apart from each other by a predetermined distance and a cylindrical probe movement coarse/fine moving unit 142b supported between the pair of support portions 142a and consisting of a vertically extendible piezoelectric element. The support portions 142a can be selectively fixed by a pair of upper inner frame fixing coarse/fine moving units 141a and a pair of lower inner frame fixing coarse/fine moving units 141b. The pair of coarse/fine moving units 141a (141b) are spaced apart from each other at an angular interval of 180° and are constituted by piezoelectric elements extendible in the inner frame 142 direction. The upper end of a cylindrical three-dimensional actuator 22 coaxial with an objective lens al is fixed on the upper support portion 142a between the inner frame 142 and the objective lens a1. This actuator 22 alternately moves the upper and lower inner frame fixing coarse/fine moving units 141a and 141b to alternately release fixing of the upper and lower support portions 142a, thereby causing the probe movement coarse/fine moving units 142b to extend/contact in the z direction, i.e., a so-called inchworm system. An edge of a circular metal frame 143 having a circular opening at its center is fixed at the lower end of the actuator 22. In this case, for example, a threadable engaging means is preferable so that the metal frame 143 can be removed from the actuator 22. A probe holder 23 consisting of cover glass is mounted in the metal frame 143 so as to seal the circular opening. At the same time, a probe 24 mounted at the center of this holder toward a sample 12 along the optical axis of the objective lens al. The sample 12 is field on a sample table 31 consisting of a stage movable in the x and y directions.

An operation of the scanning tunnel microscope shown in FIG. 15 will be described below.

The objective lens unit 140 is mounted in the revolver a2 of the optical microscope to perform a microscopic observation of a sample surface. At this time, an optical microscopic image (conventional image) is focused by coarsely moving the sample table. Since a shadow portion of the probe 24 located on the conventional image corresponds to an STM scanning range, the STM scanning range can be confirmed with the optical microscope. On the other hand, in order to observe an STM surface image, after the objective lens unit 140 is set in the in-focus position of the optical microscope, the probe 24 is finely adjusted by the carose/fine moving units 141a of the unit 140 to detect a tunnel current. Thereafter, the three-dimensional actuator 22 is moved in the same manner as in the previous embodiments to scan the sample 12 with the probe 24.

The sample table 31 for movably molding the sample may be constituted by a combination of an x-direction actuator and a y-direction actuator, or may be constituted by arranging the same actuator as the cylindrical three-dimensional actuator 22 under the sample.

The cylindrical three-dimensional actuator 22 used in the above embodiment will be described with reference to FIGS. 16A, 16B, and 16C.

Reference numeral 150 denotes a cylindrical body made of a piezoelectric material and having both open ends. Four electrodes, i.e., an X electrode 151a, a −Y electrode 151b, a −X electrode 151c, and a Y electrode 151d are circumferentially arranged in the lower portion of the outer circumferential surface of the body 150 at predetermined angular intervals. Of these electrodes, the X electrode (Y electrode) and the −X electrode (−Y electrode) are spaced apart from each other at an angular interval of 180°. One Z electrode 152 is formed at the upper portion of the outer circumferential surface of the body 150 so as to extend through the entire circumference. A rear electrode 153 serving as a ground electrode is formed on the inner circumferential surface of the body 150 to oppose the electrodes 151a, 151b, 151c, 151d, and 152. Voltages having the polarities shown in FIG. 16D are applied to the respective electrodes of the three-dimensional actuator 22 having the above arrangement to selectively scan the probe 24 in the x, y, and z directions to perform an STM observation.

Figure 17:
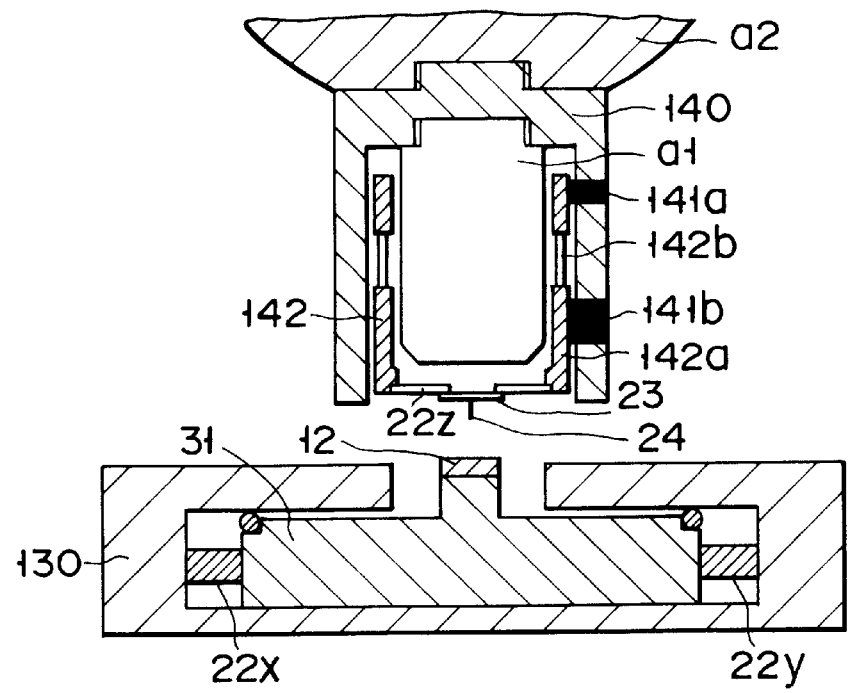
FIG. 17 is a sectional view of a scanning tunnel microscope according to the seventh embodiment.

In the seventh embodiment shown in FIG. 17, a z-direction actuator 22z extendible in only the z direction is used in place of the three-dimensional actuator 22. The actuator 22z comprises a disc-like bimorth piezoelectric element having a circular opening at its center and is fixed on the edge of a lower support portion 142a of an inner frame 142. In the same manner as in the embodiment shown in FIG. 15, a probe holder 23 consisting of cover glass is fixed in the central hole of the actuator 22z such that the optical axis of an objective lens a1 coincides with the axis of a probe 24. An x-direction actuator 22x and a y-direction actuator 22y for moving the support table 31 in the x and y directions, respectively, are arranged in a frame-like support member 130 which houses the support table 31, the upper surface of which supports a sample 12. The x- and y-direction actuators 22x and 22y are constituted by piezoelectric elements arranged between the support table 31 and the support member 130. The sample is moved in the surface direction (x-y direction) by the x-and y-direction actuators 22x and 22y, and the probe 24 is moved by the z-direction actuator 22z in the z direction, thereby performing an STM observation. In this embodiment, unlike the embodiment of FIG. 15, only one upper inner frame fixing coarse/fine moving unit 141a and only one lower inner frame fixing coarse/fine moving unit 141b are arranged, but their operations are the same as those of the embodiment of FIG. 15.

Figure 18:
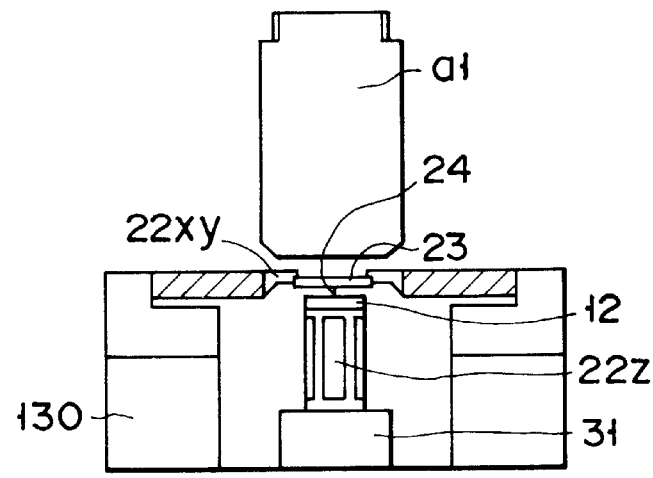
FIG. 18 is a view showing a scanning tunnel microscope of the eighth embodiment.

In the eighth embodiment shown in FIG. 18, an STM scanning mechanism is not arranged on the objective lens a1 side, but on the sample support mechanism for supporting a sample 12. In this embodiment, an xy-direction actuator 22xy having a central opening is mounted at the center of the upper surface of a frame-like support member 130. A probe holder 23 made of cover glass is mounted in the actuator 22xy so that a probe 24 extends toward the sample side. A z-direction actuator for holding the sample 12 on its upper surface and a sample table 31 for holding the actuator 22z are arranged below the probe holder 23. The z-direction actuator 22z moves the sample 12 so that a distance between the sample 12 and the probe 24 falls within the predetermined range. The three-dimensional actuator may be used in place of the z-direction actuator 22z.

The ninth embodiment will be described with reference to FIGS. 19A to 19D.

Figure 19A:
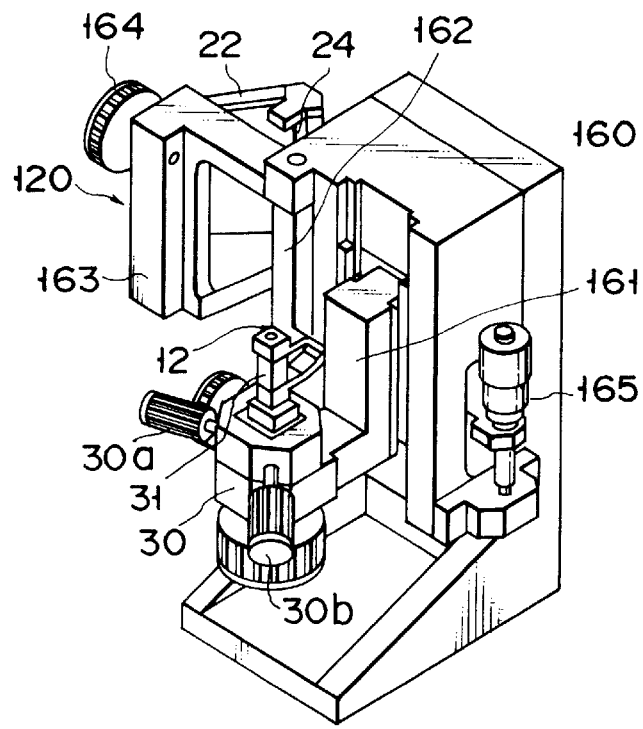
Figure 19B:
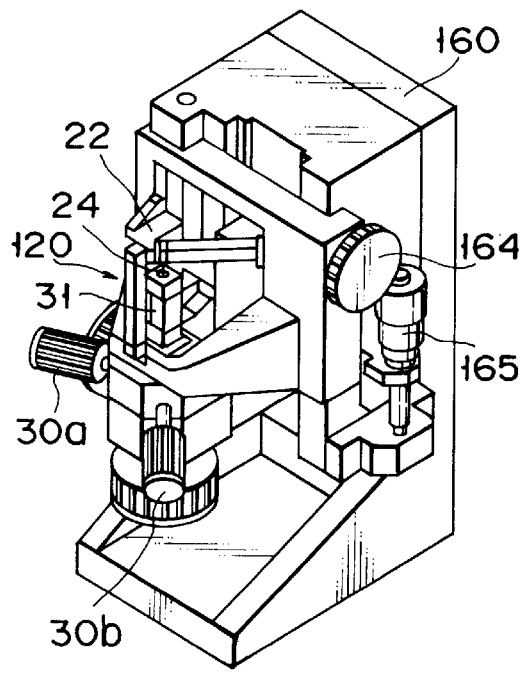

Referring to FIGS. 19A and 19B, reference numeral 160 denotes a stand. A rod-like piezoelectric element 31 also serving as a sample table and a support arm 161 for supporting a coarse moving unit 30 for coarsely moving a piezoelectric element 31 in the x and y directions extend from the front surface of the stand 160. A moving unit 165 for moving the support arm 161 in the z direction with respect to the stand 160 is also arranged on the stand 160. The upper and lower ends of a rotating shaft 162 extending in the vertical direction are rotatably supported at a corner portion of the front surface of the stand 160. A tunnel scanning unit 120 is arranged on the rotating shaft 162 so as to be rotated together therewith. The tunnel scanning unit 120 comprises a support 163 extending from the rotating shaft. A three-dimensional actuator 22 is fixed on the support 163. The actuator 22 comprises a tripod actuator consisting of three rod-like piezoelectric elements perpendicular to each other and connected to each other at their proximal ends. A probe 24 extends downward from the proximal portions of the piezoelectric elements. A lock means 164 is arranged in the support 163 to lock the tunnel scanning unit 120 to the stand 160 when the tunnel scanning unit 120 is pivoted from an STM nonmeasurement position shown in FIG. 19A to an STM measurement position shown in FIG. 19B. The lock means 164 comprises a lock screw threadably engaged with the support 163. The distal end of the lock screw is urged against the side surface of the stand 160, thereby achieving locking. The coarse moving unit 30 comprises an x table for supporting the sample table 31, a y table, and operation knobs 30a and 30b respectively for the x and y tables.

Figure 19C:
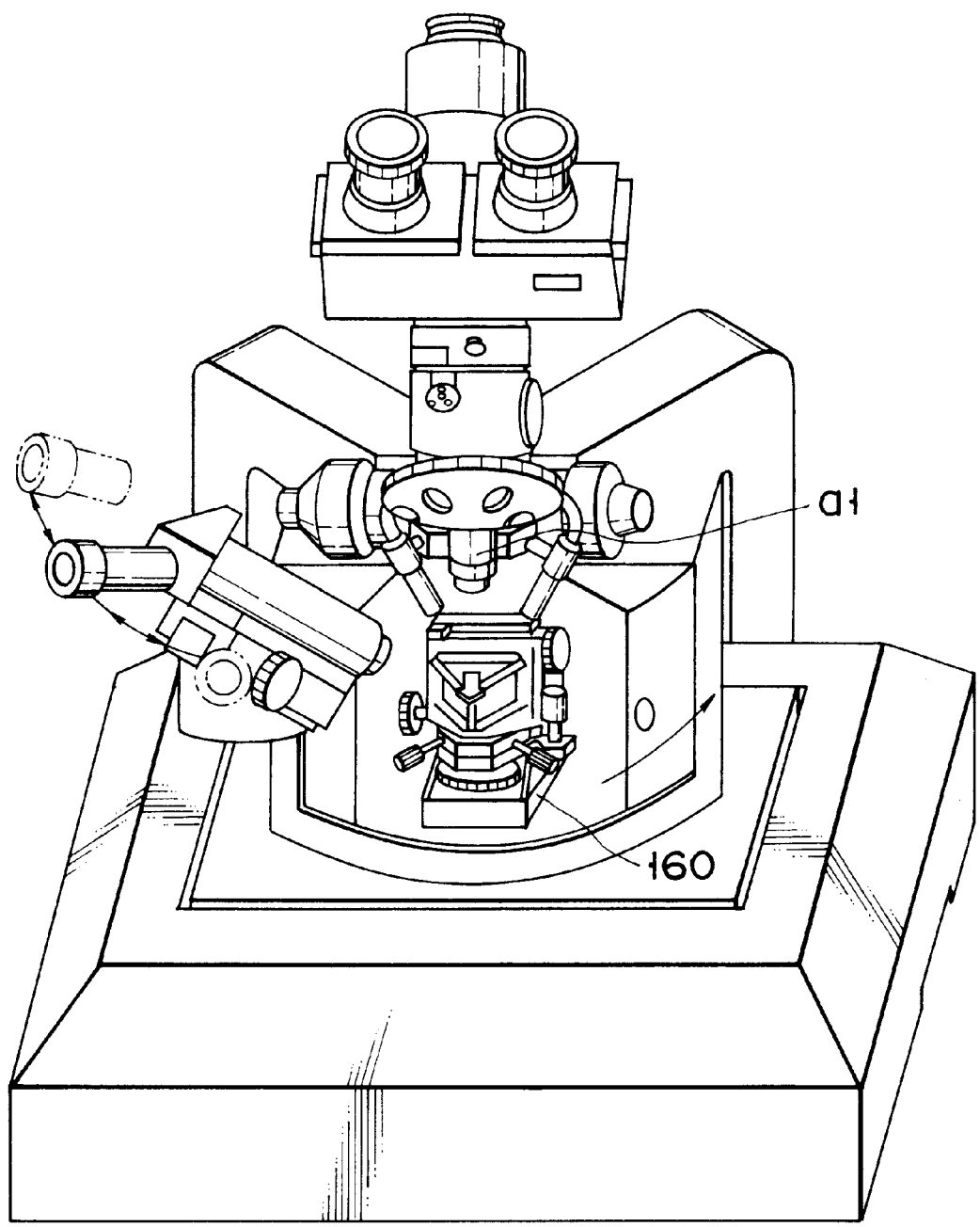

FIG. 19C shows a state wherein the stand 160 is assembled in a known metallurgical microscope. In this case, the optical axis of an objective lens a1 of the microscope is set to be aligned with the axis of the probe 24, and both the optical observation and the STM observation are performed.

At first, the tunnel scanning unit 120 is set at a position offset from the sample 12 (FIG. 19A), and the operation knobs 30a and 30b are rotated to determine an STM observation position within the horizontal plane while the sample 12 is kept observed with the metallurgical microscope. When an operation knob 165 is rotated to determine a height and hence an in-focus position (the in-focus position is a substantially scanning position of the probe 24). A marker (e.g., +) is formed at the same position as that of the probe 24. This position is determined when the tunnel scanning unit 120 is set in the scanning state. In addition, since an STM scanning range can also be confirmed, the operator can accurately check setting of a sample position to be scanned and a material in the scanning range while observing through the metallurgical microscope.

After the scanning position is determined, the tunnel scanning unit 120 is fixed on the stand 160, and an STM image is measured.

Figure 19D:
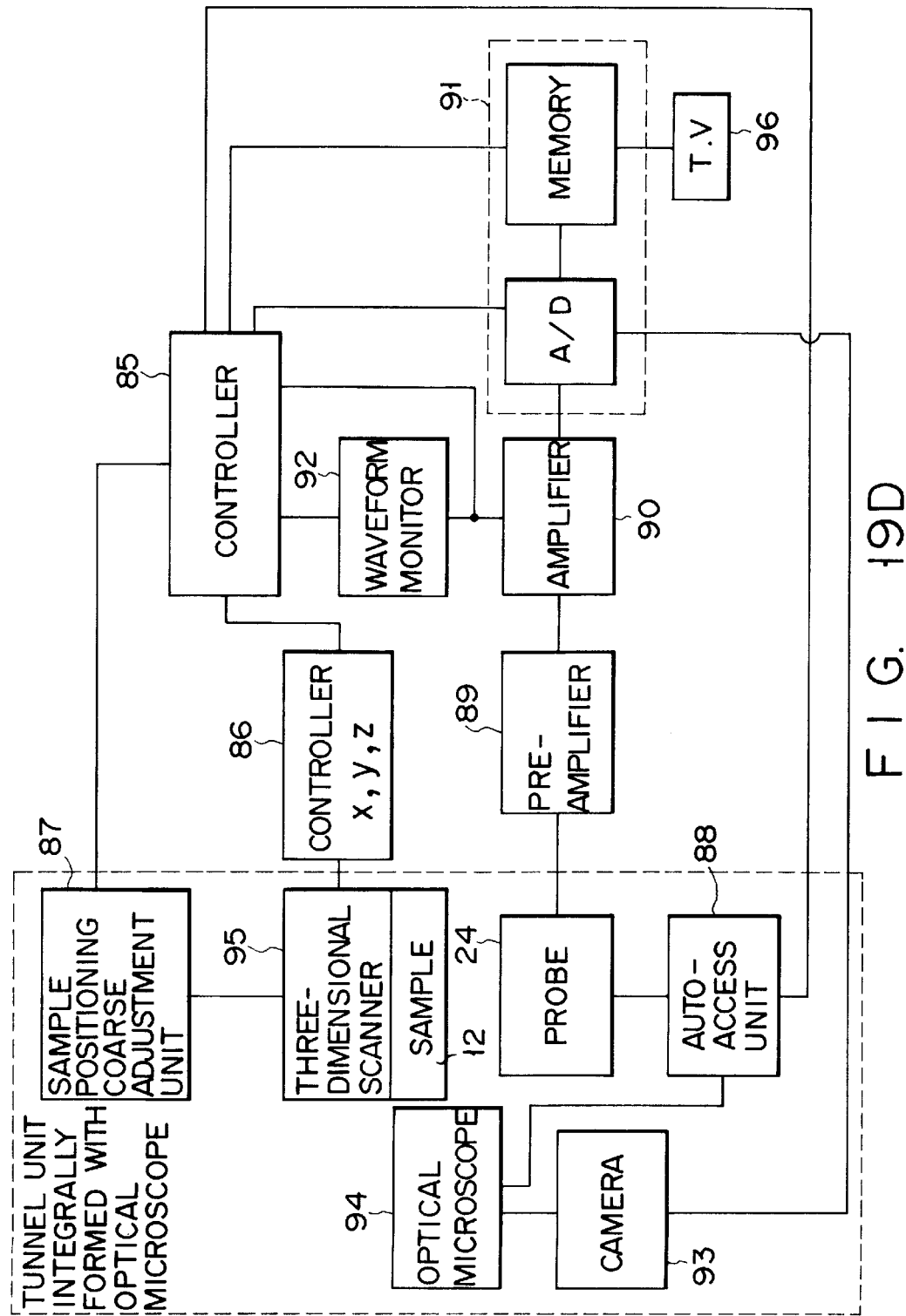
FIG. 19D is a block diagram showing an arrangement of an STM measurement system.

FIG. 19D is a block diagram showing an arrangement of the STM measuring system.

Reference numeral 85 denotes a controller. The controller 85 incorporates an input interface 91 and an output interface. The controller 85 is connected to a CRT graphic display, a frame memory, a plotter or printer as a recording unit, and the like. A measurement area selection button, and an input unit such as a mouse serving as a control box are connected to the input terminals of the controller 85. An X,Y,Z-position controller 86, an xy-direction sample positioning coarse moving unit 87, and an auto-access unit 88 are connected to the output terminals of the controller 85.

In the tunnel unit integrally formed with the optical microscope, a tunnel current obtained from the probe 24 is amplified by a preamplifier 89 and an amplifier 90, and the amplified signal is supplied to the controller 85 through the input interface 91.

An observation image obtained by an optical microscope (an optical microscope obtained by incorporating the tunnel unit in an objective lens portion) integrally and optically connected to the STM tunnel unit is picked up by a video camera 93, and the image pickup signal is supplied to a video monitor 93. The image pickup signal is also supplied to the controller 85 through the input interface 91.

A method of operating the apparatus of this embodiment and its operation concentrated on the operation of the above controller will be described below.

After the apparatus is powered, the following operations are performed.

I. The sample 12 is fixed on the sample table, and a tunnel bias voltage application electrode is attached thereto.

II. In order to determine a position of an STM image observation portion, the sample is observed with an optical microscope 94. At this time, the optical microscope is focused by an automatic focusing mechanism. A method of focusing the microscope is to use a knife etch method. A change in optical image caused by out of focus is picked up by the video camera 93 mounted on the eyepiece lens portion and is input to the controller 85. An automatic focusing mechanism control signal is input from the controller 85 to the automatic focusing unit to control a relative position between the sample and the objective lens portion, thereby focusing the optical microscopic image.

The relative position between the objective lens and the sample is set in the in-focus position by using the automatic focusing mechanism to set the distance between the sample and the STM probe mounted at the distal end of the objective lens to be as close as a predetermined value (about 50 $\mu$m).

When the optical focusing operation is completed, positioning of the STM observation portion is performed.

A sample surface portion subjected to STM observation is aligned with the marker (the STM probe is present at this position) located at the center of the optical microscopic image. At this time, switches on the controller are operated to adjust the sample position. At this time, the X,Y-direction positioning signals output from the sample positioning coarse moving unit 87 to determine an xy position of the sample and angles of the $\Theta$(xy plane), $\Phi$(plane), Y(yz plane) directions.

III. After the STM observation position is determined as described above, the STM probe is caused by the auto-access unit 88 to come close to a position where a tunnel current can be observed.

When a relative position between the STM probe and the sample comes close to a position having a predetermined value upon optical focusing, a bias voltage is applied to the sample, and a tunnel current flowing between the sample and the probe is amplified by the preamplifier and the amplifier. The amplified signal is input to the controller. An auto-access unit control signal is input from the controller to the auto-access unit to adjust the distance between the sample and the probe to have a predetermined value.

Even when a tunnel current is excessively increased, the probe can be separated from the sample by using the auto-access mechanism. Therefore, there is no danger of bringing the probe into contact with the sample.

By using the two-step auto-access mechanism which performs optical auto-access and senses the tunnel current, a period required for causing the probe to come close to the sample can be shorted.

IV. The sample inclination is adjusted to be parallel to the surface of the objective lens by, e.g., a goniometer on the sample positioning coarse moving unit (the probe is adjusted to be perpendicular to the sample surface).

The inclination adjustment of the sample is performed by the following two steps.

a. A control signal is supplied from the controller to the sample positioning coarse moving unit 87 so that an optical microscopic image picked up by the video camera is focused through the entire field. The sample inclination is thus corrected.

b. A tunnel current signal obtained upon scanning of a three-dimensional scanner 95 in a wide range (about 10 $\mu$m) is amplified. The amplified signal is input to a waveform monitor 92. By using two methods, i.e., an optical method wherein a control signal is input from the controller 95 to the sample positioning coarse moving unit 87 such that an output from the waveform monitor 92 is set constant (i.e., the x- and y-axis scanning signals and identical frequency components are set zero), thereby correcting the sample inclination, and a tunnel current sensing method, the sample inclination is corrected. Therefore, as compared with a method of sensing only the tunnel current, the sample inclination can be corrected within a short period of time.

V. The three-dimensional scanner 95 is scanned in the x and y directions, and an STM image is measured while a z-direction position is controlled so that a tunnel current is kept constant.

In order to obtain an STM image in a wide range (substantially the same range as that of the optical microscopic image), STM images are connected by using the sample positioning coarse moving unit 87 (STM images in narrow ranges are sequentially measured while the scanning position on the sample surface is sequentially changed and are connected in accordance with software).

An apparatus similar to the apparatus of the embodiment shown in FIG. 6 will be described with reference to FIG. 20.

Figure 20:
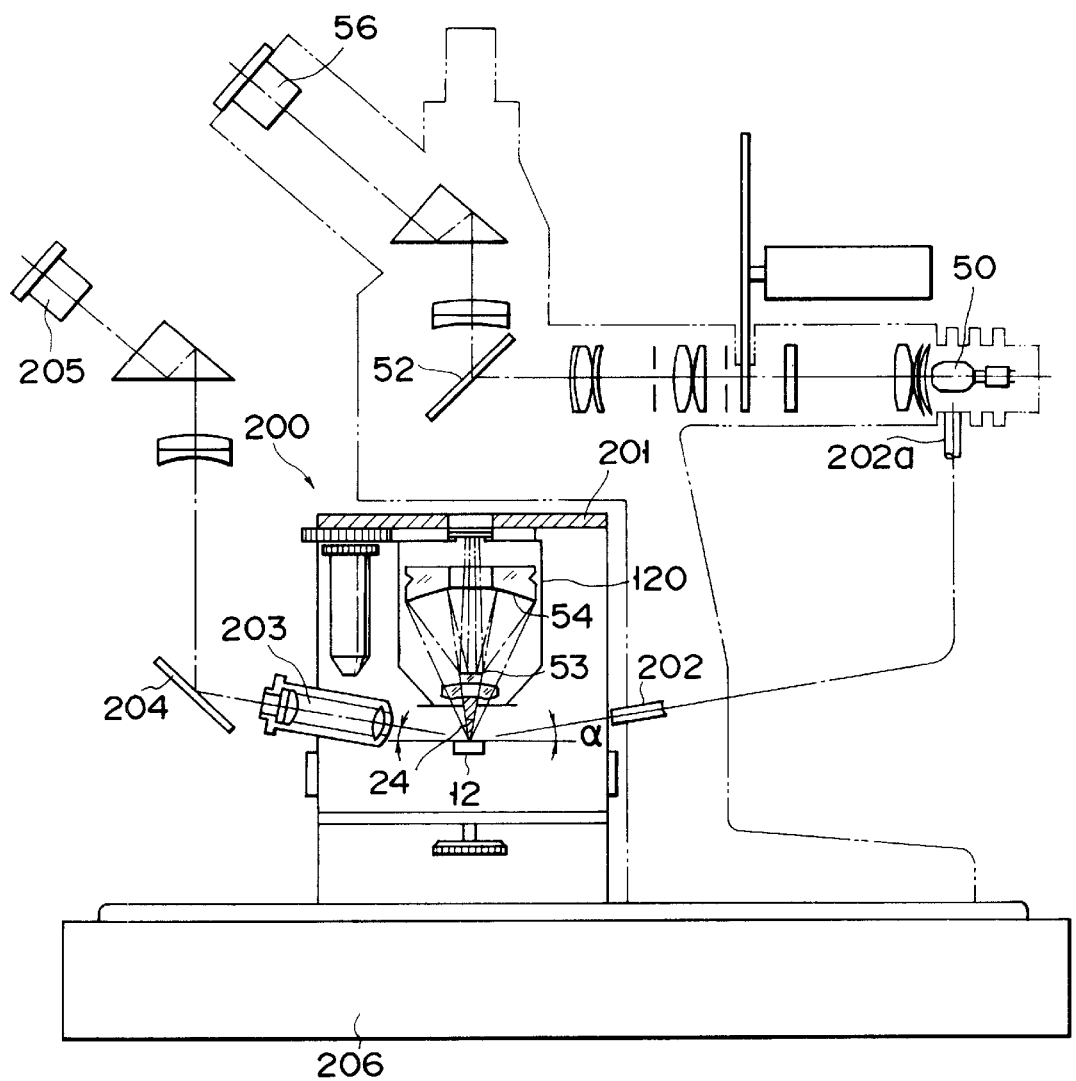
FIG. 20 is a view showing an optical system of a scanning tunnel microscope of the tenth embodiment.

The same reference numerals as in FIG. 6 denote substantially the same parts having the same functions in the embodiment of FIG. 20, and a detailed description thereof will be omitted.

In this embodiment, an observation means for observing a very small interval between a measurement surface of a sample 12 and a distal end of a probe 24 is arranged as follows.

Referring to FIG. 20, reference numeral 200 denotes a measurement unit obtained by incorporating a sample support mechanism and an objective lens unit 120 in a unit frame 201. One end of an optical fiber (cold fiber) 202 for guiding light to the sample 12 is located on one side of the unit frame 201. An auxiliary objective lens 203 is arranged on the other side of the unit frame 201 to receive light reflected by the sample 12 through the optical fiber 202. One end of the optical fiber and the auxiliary objective lens 203 can be inclined on the vertical plane in a range ($\alpha$) of about 20° from the observation surface of the sample 12 with respect to the center of the surface of the sample 12. The other end 202a of the optical fiber 202 extends near a light source 50 of an optical microscope. As a result, light from the light source 50 is guided to the sample 12 through an illumination system of the optical microscope and at the same time to the sample 12 through the optical fiber 202. An auxiliary eyepiece lens 205 is arranged on the rear-side optical axis of the auxiliary objective lens 203 through a rotatable reflecting mirror 204. Reflected light from the auxiliary objective lens 203 is received through the reflecting mirror 204, thereby visually checking an interval between the observation surface of the sample 12 and the distal end of the probe 24 through the auxiliary eyepiece lens 205. As a result, while the measurement is being performed, the probe 24 can come close to the sample 12, thereby preventing damage to the sample 12 and the probe 24 upon contact therebetween.

Referring to FIG. 20, reference numeral 206 denotes a vibration preventive table on which the measurement unit 200 is placed.

An arrangement of the measurement unit 200 will be described with reference to FIGS. 21A to 21D.

The unit frame 201 has an upper frame 201a, a lower frame 201b, a pair of opposite side frames 201c. A circular opening 201d is formed at the center of the upper frame 201a to transmit light from the light source 50 into the unit frame 201 and light from the unit frame 201 toward the eyepiece lens 51. A disc-like objective revolver 211 is rotatably mounted by a rotating shaft 211a on the inner surface of the upper frame 201a. Two objective lenses a1 having different magnifications and one objective lens unit 140 are arranged in the objective revolver 211 at equal intervals. These intervals are determined such that when the objective lenses a1 and the unit 140 are selectively moved to the opening 201d, the axis of the moved lens or unit is aligned with the axis of the opening 201d. A coarse moving screw 213, one end of which extends inside the unit frame 201, is externally threadably engaged with the center of the lower frame 201b of the unit frame 201. A coarse moving table 215 is supported at the extended end of the coarse moving screw such that the coarse moving table 215 is guided and vertically moved (z direction) through a coarse moving ball 214 by two pairs of guide rails 215a arranged at corners of both ends upon rotation of the coarse moving screw 213. An xy-direction table 216 having an externally scanned x-direction adjustment knob 216a and an externally scanned y-direction adjustment knob 216b (FIG. 21D) are placed on the upper surface of the coarse moving table 215 so as to be movable in the surface direction (x and y directions) with respect to the coarse moving table. The coarse moving table 215 and the xy-direction table 216 are engaged by a projection and a recess with a play formed in the surface direction. One spring 216c for biasing the xy-direction table 216 with respect to the coarse moving table 215 in one direction is arranged between the engaging side surfaces of the coarse moving table 215 and the xy-direction table 216. A rectangular groove 216a having both open ends is formed on the upper surface of the central portion of the xy-direction table in its widthwise direction. A middle fine moving plate 217 is inserted into the rectangular groove 216a. A first actuator 218 extendible in the z direction is fixed at one end of the XY table 216 in the longitudinal direction. A first fine moving pin 219 engaged with a recess formed on the lower surface at one longitudinal end of the middle fine moving plate 217 abuts against the upper end of the actuator 218. A first stationary pin 220 is inserted between the xy-direction table 216 and the other end of the middle fine moving plate 217. Upon extension/contraction of the first actuator 218, the middle fine moving plate 217 is pivotal about the first stationary pin 220 on the vertical plane with respect to the xy-direction table 216. A high fine moving plate 221 is arranged on the middle fine moving plate 217. A second actuator 222 extendible in the z direction extends from the other longitudinal end of the middle fine moving plate 217. A second fine moving pin 223 engaged with a recess formed on the lower surface of the other longitudinal end of the high fine moving plate 221 abuts against the upper end of the actuator 222. A second stationary pin 224 supported by the inner wall of the rectangular groove 216a is inserted between one end of the high fine moving plate 221 and a portion near one side of the center of the middle fine moving plate 217. Upon extension/contraction of the second actuator 222, the high adjustment plate 221 is proval about the second stationary pin 224 on the vertical plane with respect to the middle fine moving plate 217. An xy-direction actuator 22xy is supported on the upper surface near one end of the high fine moving plate 221. The sample 12 is placed on the actuator 22xy. The xy-direction actuator 22xy moves the sample 12 in the x and y directions and cooperates with a z-direction actuator 22z (to be described later) to perform an STM observation. In this embodiment, a distance between the sample 12 and the second fine moving pin 223 is set to be ten times the distance between the second stationary pin 224 and the sample 12. That is, a lever ratio of the high fine moving plate 221 is set to be 10:1. The distance between the first fine moving pin 219 and the first stationary pin 220 is set to be twice the distance between the sample 12 and the second fine moving pin 223. For this reason, when the second actuator 222 is moved upward by 1 $\mu$m, the surface of the sample 12 comes close to the probe 24 by 1 $\mu$m×$\frac{1}{10}$=0.1 m. When only the first actuator 218 is moved upward by 1 $\mu$m without operating the second actuator 222, the surface of the sample 12 comes close to the probe 24 by 1 $\mu$m×$\frac{1}{20}$×$\frac{1}{10}$=0.0005 $\mu$m. That is, the second actuator 222 can provide intermediate fine movement to the sample 12, and the first actuator 218 can provide very fine movement thereto. Spring seats 230 and 231 are fixed between both ends of the pair of side frames 201c of the unit frame 201. A compression spring 232 for always biasing one end of the middle fine moving plate 217 is inserted between one spring seat 230 and the upper surface of one end of the middle fine moving plate 217. At the same time, a compression spring 233 for always biasing the other end of the high fine moving plate 217 is inserted between the other spring seat 231 and the upper end of the other end of the high fine moving plate 221. The respective component parts of the measurement unit 200 are firmly fixed in the unit frame 201, thus providing high earthquake resistance. The members such as the unit frame 201 are made of amber having a small thermal expansion coefficient and are made compact, thus substantially minimizing thermal influences.

The objective lens unit 140 will be described with reference to FIG. 22.

Figure 22:
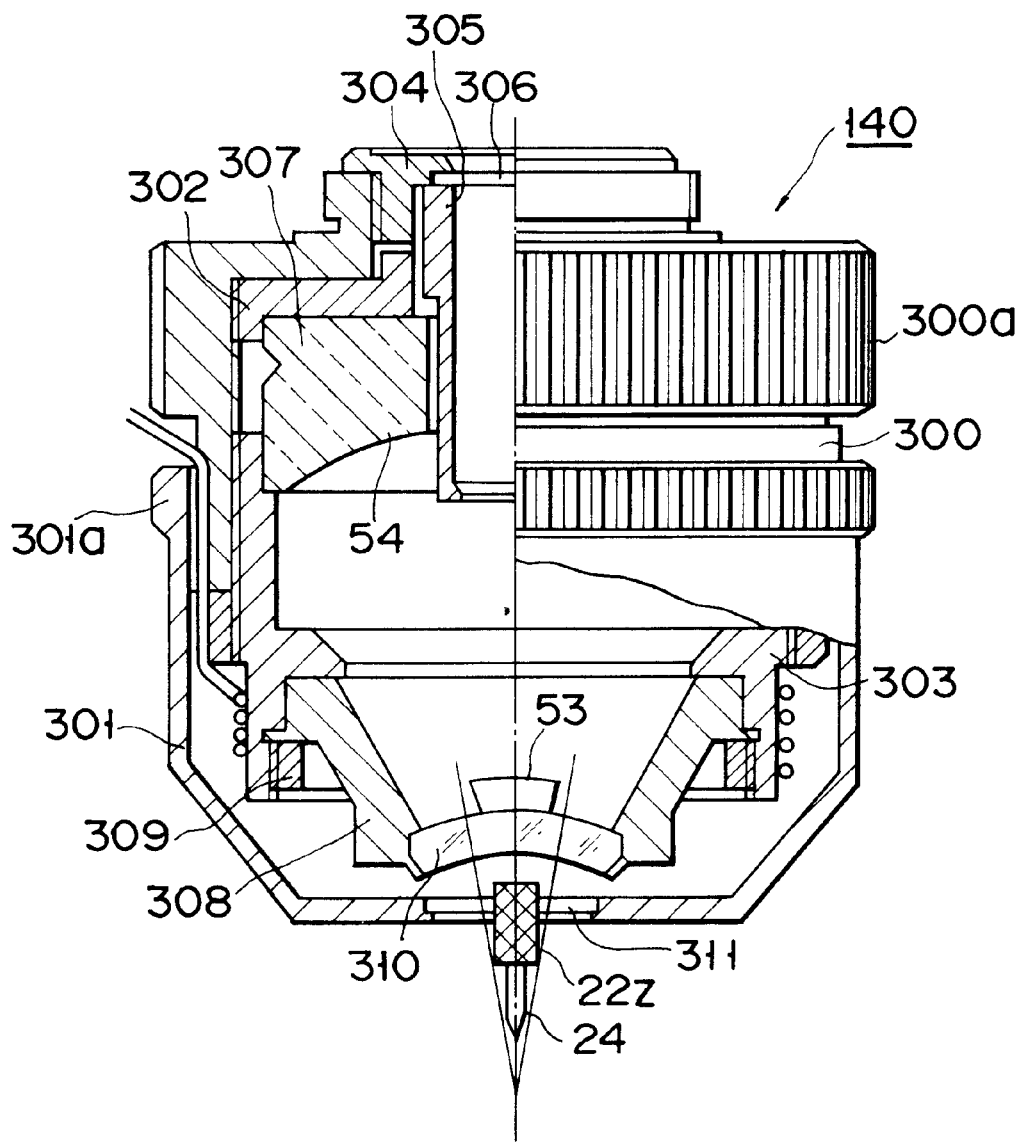
FIG. 22 is a partially cutaway side view of an objective lens unit used in the measurement unit.

Referring to FIG. 22, reference numeral 300 denotes a cylindrical upper housing having a detaching knurled portion 300a on its circumferential surface. A male thread is formed on the lower circumferential portion of the upper housing 300. This male thread has a knurled portion 301a on its outer circumferential surface. A female thread formed on the inner circumferential surface of the upper portion of a cylindrical lower housing 301 having an upper open end is threadably engaged with the above male thread. The upper and lower housings 300 and 301 are detachably coupled to each other by threadable engagement. A female thread is formed on the inner circumferential surface of the upper housing 300. An upper support cylinder 302 and a lower support cylinder 303 vertically spaced apart therefrom by a predetermined distance are threadably engaged with this female thread through male threads formed on the outer circumferential surfaces of the cylinders 302 and 303. A set screw 304 is threadably engaged with the female thread formed on the cylindrical extended portion of the upper end of the upper housing 300 through a male thread formed on the outer circumferential surface of the set screw 304. The set screw 304 has upper and lower open ends, and inward and outward flanges at its upper end. The set screw 304 is cylindrical and a female thread is formed on its inner circumferential surface. A male thread formed on the upper outer circumferential portion of a cylindrical light guide member 305 having upper and lower open ends is threadably engaged with the female thread of the set screw 304. A first lens 306 is fastened and fixed between the inward flange of the set screw 304 and the upper end of the light guide member 305. A second lens 307 having a through hole at its central portion is fastened and fixed between the lower surface of the upper support cylinder 302 and the inner circumferential surface of the lower support cylinder 303. The upper portion of a lens mounting barrel 308 is inserted into the lower portion of the lower support cylinder 303 and is fixed by a fastening ring 309. A third lens 310 is mounted in the small-diameter lower end portion of the lens mounting barrel 308. A concave mirror 54 is formed on the lower surface of the second lens, and a convex mirror 53 is formed at the central portion of the upper surface of the third lens. An opening is formed at the central portion of the lower end of the lower housing 301. A transparent member such as a support plate 311 made of, e.g., quartz glass is fitted in this opening. The z-direction actuator 22z is mounted at the central portion of the support plate 311 so as to extend downward. A probe 24 is mounted at the distal end of the actuator 22z so as to extend downward. The first to third lenses 306, 307, and 310, the concave mirror 54, the convex mirror 53, the probe 24, and the z-direction actuator 22z are coaxially arranged. A measurement unit 200 mounted with the unit 140 is mounted in the optical microscope shown in FIG. 20, and observations of the conventional image and the STM image are the same as those of the previous embodiments, and a detailed description thereof will be omitted.

A probe-sample interval measurement unit consisting of the optical fiber 202 and the auxiliary objective lens 203 will be described with reference to FIG. 23.

Figures 21A, 21B:
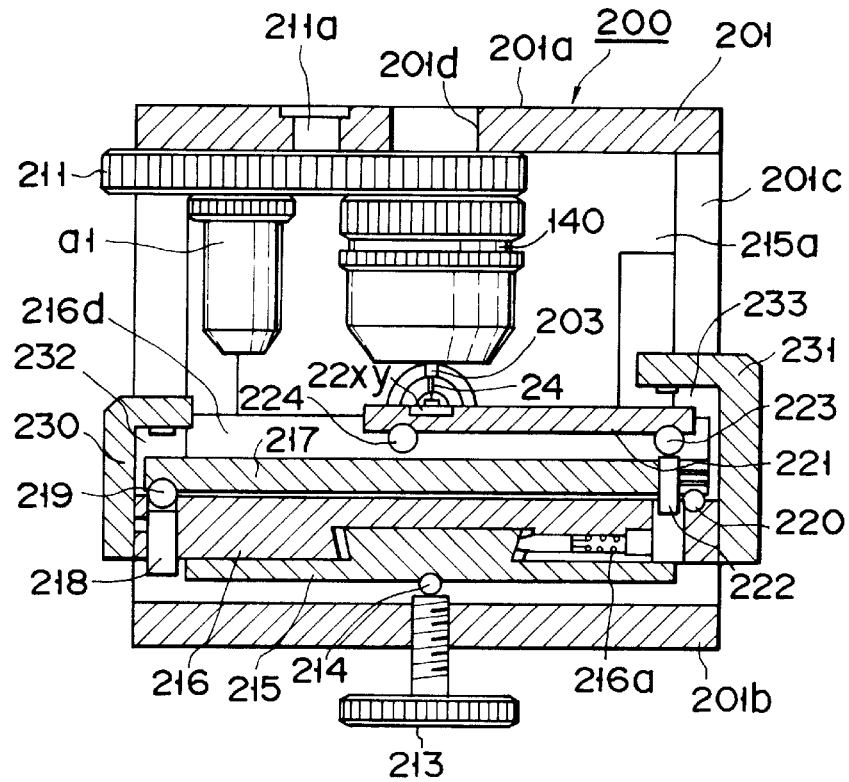
Figure 23:
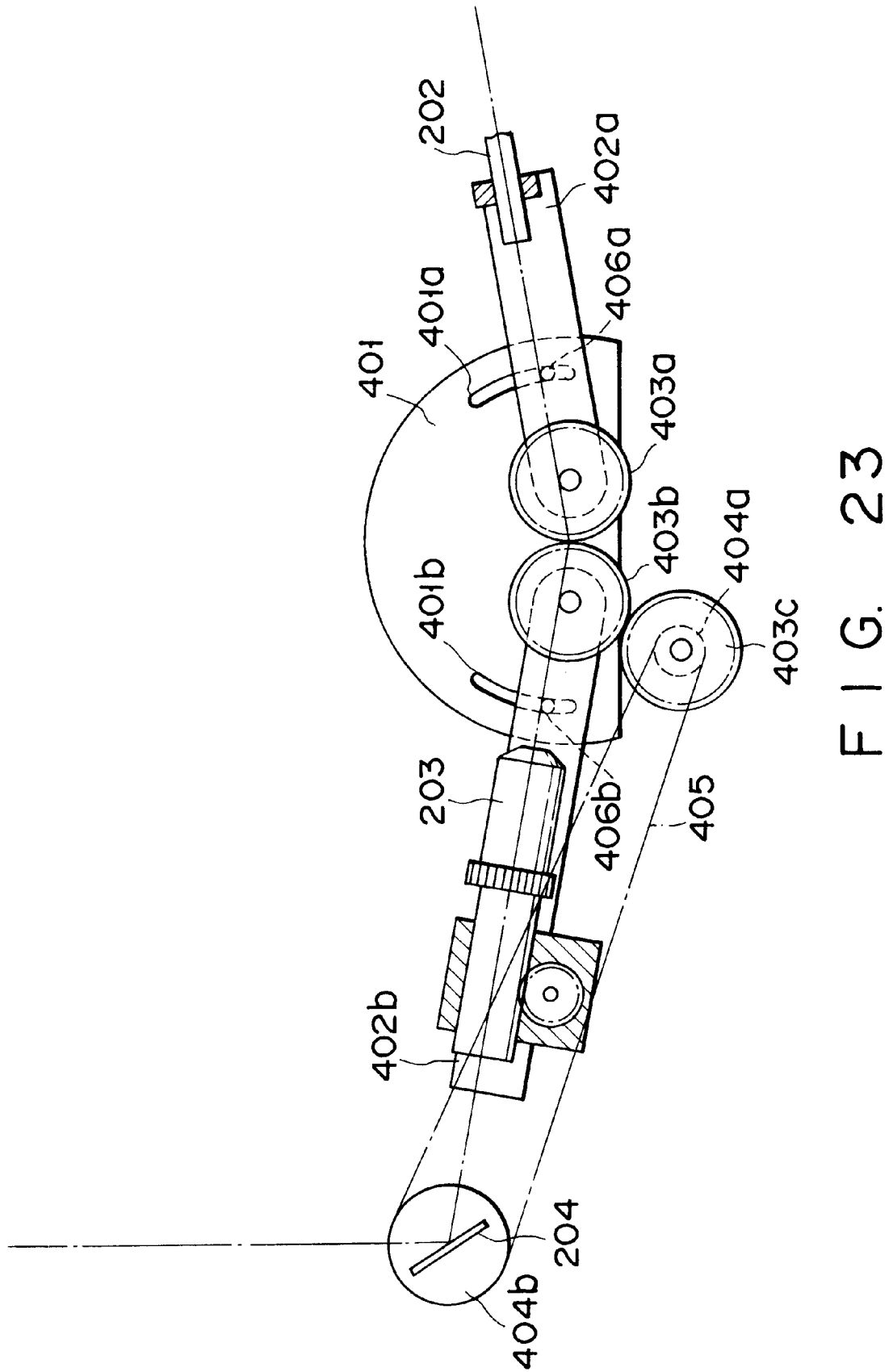
FIG. 23 is a partially cutaway side view showing an interval measurement unit used in the tenth embodiment.

Referring to FIG. 23, reference numeral 401 denotes a guide plate fixed in the unit frame 201 (FIG. 21A) along the vertical plane. First and second arcuated guide grooves 401a and 401b symmetrically extending along the circumferential surface of the guide plate 401. One end of each of first and second pivot arms 402a and 402b is located in front of the guide plate 401. A one-end portion of the optical fiber 202 is fixed at the other end of the first arm 402a to be pivotal together and parallel with the arm 402a. An auxiliary objective lens 203 is mounted at the other end of the second arm 402b so as to be pivotal together and parallel with the arm 402b. The auxiliary objective lens 203 is coupled to the arm 402b through a rack-pinion mechanism so as to be linearly moved by the pinion along the optical axis. Gears 403a and 403b are respectively fixed to one-end portions of the first and second arms 402a and 402b. A third gear 403c is meshed with the second gear 403b. The first to third gears 403a, 403b, and 403c are rotatably supported by the unit frame 201 (FIG. 21A). The first and second arms 402a and 402b are pivoted about their axes within the vertical plane upon pivotal movement of the gears 403a and 403b. A first pulley 404a is coaxially fixed on the third gear 403c so as to be pivotal together with the gear 403c. A second supply 404b is mounted on a reflecting mirror 204 arranged on the light emerging side of the auxiliary objective lens 203 so as to be rotated together with the reflecting mirror 204. An endless belt 405 is looped between the first pulley 404a and the second pulley 404b. Engaging pins 406a and 406b, distal ends of which are located in the guide grooves 401a and 401b, extend from the first and second arms 402a and 402b and are guided along these guide grooves, respectively.

In the interval measurement unit having the above arrangement, when the auxiliary objective lens 203 is pivoted, the optical fiber 202 is pivoted by the same amount as that of the auxiliary objective lens 203 through the gears 403a and 403b and the arms 402a and 402b. As a result, light reflected by the sample upon incidence of light from the optical fiber 202 is always and effectively guided to the auxiliary objective lens 203. Upon pivotal movement of the auxiliary objective lens 203, the reflecting mirror 204 is also pivoted through the gears 403b, 403c, the pulleys 404a and 404b, and the endless belt 405. As a result, light emerging from the auxiliary objective lens 203 is guided to the auxiliary eyepiece lens 205 (FIG. 20) by the reflecting mirror 204 at any pivotal position of the auxiliary objective lens 203. Therefore, the auxiliary objective lens 203 is pivoted to come to a position where an interval between the probe and the sample can be easily measured, thereby performing measurements.

Figure 24A:
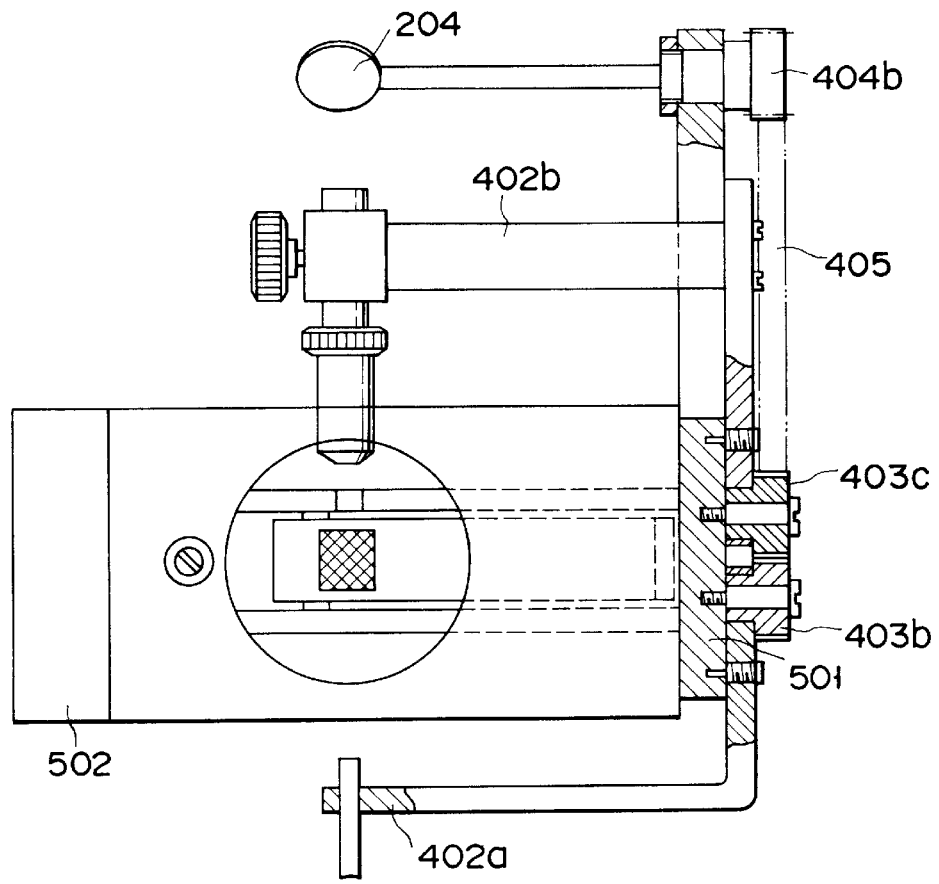
Figure 24B:
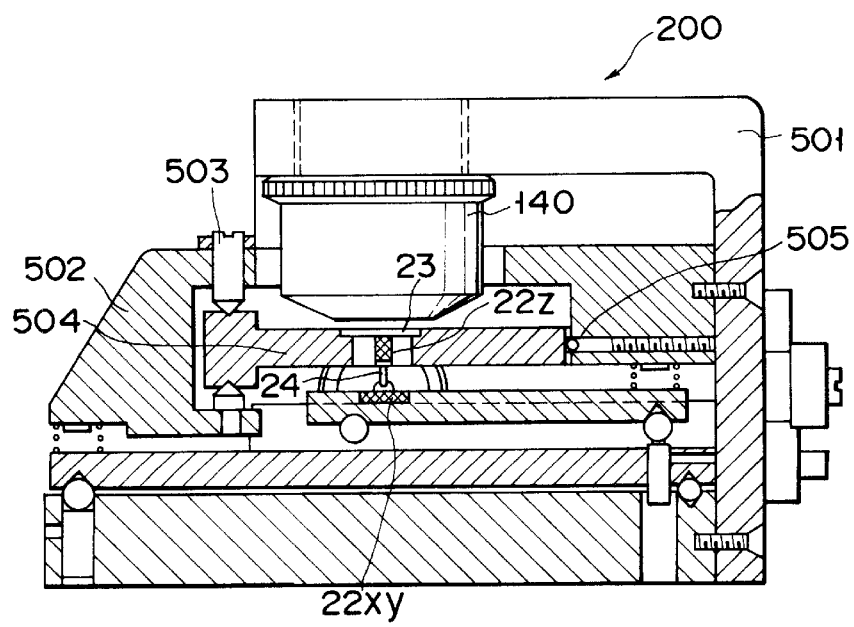
Figure 24C:
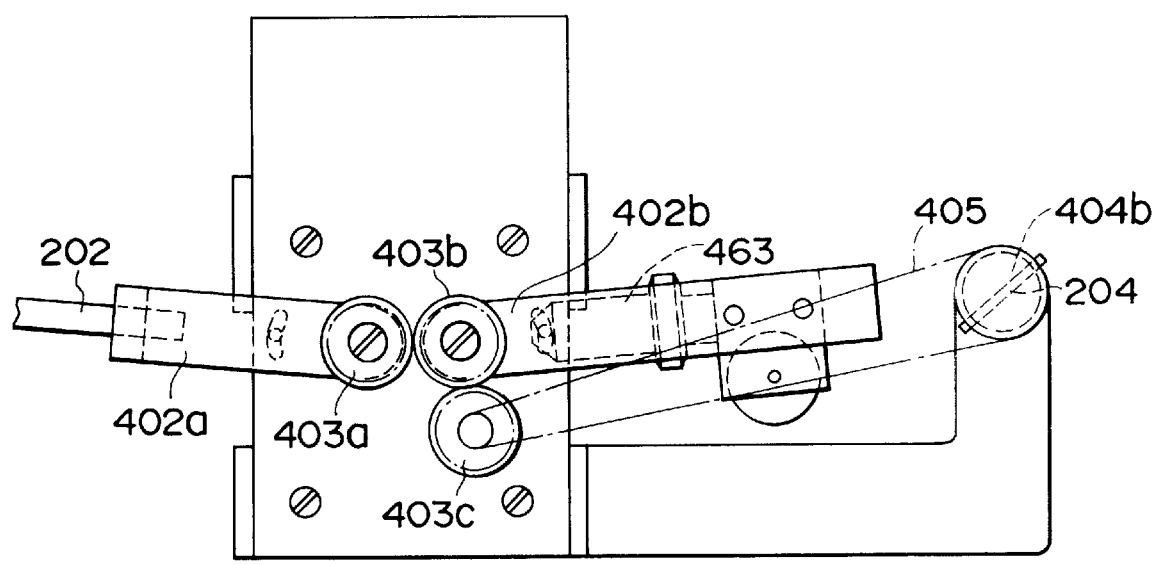

FIGS. 24A to 24C show a modification of the measurement unit 200 shown in FIG. 21A and the interval measurement unit shown in FIG. 23. In this modification, the unit 140 is supported by a support arm 501 fixed on a microscope (not shown). The actuator and the probe 24 are not mounted on the unit 140, unlike the previous embodiment. Reference numeral 502 denotes a stationary member. One end of a pivot plate 504 is fixed to the stationary member 502 through a pivot shaft 503 within the horizontal plane between a position where the pivot plate 504 is located below the unit 140 and a position where the pivot plate 504 is offset from the position where the pivot plate 504 is located below the unit 140. A through hole is formed at the central portion of the pivot plate 504. A probe holder 23 made of, e.g., cover glass is formed to cover the through hole. The probe 24 is fixed in the probe holder 23 to extend downward, i.e., extend toward the sample 12 direction through the z-direction actuator 22z. The sample is supported to extend below the probe 24 by the xy-direction actuator 22xy. Reference numeral 505 denotes a click mechanism for holding the pivot plate 504 to the illustrated STM observation position. In this modification, the first and second gears 403a and 403b for synchronously pivoting the optical fiber 202 and the auxiliary objective lens 203 and the third gear 403c for pivoting the reflecting mirror 204 are pivotally supported on the support arm 501.

In the present invention, an optical microscope except for a metallurgical microscope exemplified in the above embodiments may be used as a microscope for observing the STM scanning range. For example, a polarizing microscope, a Nomarski differential interference microscope, a fluorescence microscope, an infrared microscope, a stereomicroscope, a geometric measurement unit, a microscopic photometric system, and the like may be used.

INDUSTRIAL APPLICABILITY

In a scanning tunnel microscope according to the present invention, the probe of the STM system (tunnel scanning unit) and the eyepiece optical member of the optical microscope are moved in the axial direction (z direction) with respect to the observation surface of the sample, and both the images can be observed and can be easily compared with each other, thus providing a practical advantage.

What is claimed is:

1. A scanning tunnel microscope comprising:

a sample table for holding a sample, a probe held to be spaced apart from said sample by a predetermined interval in an axial direction, an actuator for three-dimensionally driving said sample and said probe relative to each other, an objective lens of a transmission/refraction system which has a central through hole through which said probe is movable, and an eyepiece optical member for receiving light from said sample through said objective lens.

2. A scanning tunnel microscope comprising:

means for holding a sample, a probe located on a side opposite to a sample surface and held to be spaced apart from said sample surface, actuator means for relatively and three-dimensionally driving said sample and said probe, and an observation optical system having an eyepiece optical member which is located to oppose said sample surface, is movable in a vertical direction with respect to said sample surface, and has an objective optical member having an optical axis substantially aligned with an axis of said probe with respect to said sample surface, and an eyepiece optical member for receiving light reflected by said sample surface through said objective optical member, said observation optical system being able to allow an observation of said sample surface through said eyepiece optical member.

3. A scanning tunnel microscope according to claim 2, wherein said objective optical member comprises a concave mirror for receiving the light reflected by said sample, and a convex mirror for guiding the reflected light from said concave mirror to said eyepiece optical member, said concave and convex mirrors being arranged substantially coaxially with said probe.

4. A scanning tunnel microscope according to claim 2, wherein said probe is located between said objective optical member and said sample to mechanically separate at least said probe from said eyepiece optical member, thereby eliminating an influence of said probe on sample measurement which is caused by vibrations from an eyepiece optical member side.

5. A scanning tunnel microscope comprising:

means for holding a sample;

a probe located between a surface of the held sample and an objective optical member, and held spaced from the sample surface;

actuator means for relatively and three-dimensionally driving said sample and said probe; and a sample surface observation optical system which includes at least one objective optical member having an optical axis substantially aligned with a central axis of said probe with respect to the sample surface, arranged in opposition to the sample surface, and being vertically movable with reference to the sample surface.

6. A scanning tunnel microscope according to claim 5, further comprising a sample geometry-measuring optical system arranged in an optical path of the light reflected by said sample through said objective optical member, thereby measuring a geometry of an observation surface of said sample.

7. A scanning tunnel microscope according to claim 6, wherein said sample geometry-measuring optical system and said observation optical system are arranged on an optical axis of the light reflected by said sample through said objective optical member, and wherein an objective optical member common in said sample geometry-measuring optical system and said observation optical system comprises a reflection objective lens to be made of a concave mirror and a convex mirror.

8. A scanning tunnel microscope according to claim 5, wherein said sample surface observation optical system includes a camera for photographing light reflected by the sample surface.

9. A scanning tunnel microscope according to claim 5, wherein said observation optical system includes:

a plurality of objective optical members; and means for switching the objective optical members from one to another.

10. A scanning tunnel microscope according to claim 9, wherein said objective optical members include one of a polarization microscope, a Nomarski differential interference microscope, a fluorescence microscope, and a stereomicroscope.

11. A scanning tunnel microscope according to claim 5, further comprising:

a light source for irradiating light from a side of said probe; and a side observation optical system for observation of a sample surface which is located in the vicinity of said probe and which is irradiated with the light irradiated by said light source.

12. A scanning tunnel microscope according to claim 5, wherein said actuator means is fixed to a sample table.

13. A scanning tunnel microscope according to claim 5, wherein said actuator means includes:

a first actuator for relatively driving said sample and said probe in X and Y directions; and a second actuator for relatively driving said sample and said probe in a Z direction;

one of said actuators being fixed to an outer frame of an objective lens, and the other of said actuators being fixed to a sample table.

14. A scanning tunnel microscope according to claim 5, wherein said actuator means includes:

a three-dimensional actuator for three-dimensionally driving at least one of said sample and said probe on a fine scale; and a coarsely-driving actuator for driving at least of said sample and said probe on a coarse scale.

15. A scanning tunnel microscope comprising:

a probe, support means for supporting said probe such that an optical axis of an objective optical member of an optical microscope is substantially aligned with an axis of said probe, and actuator means for relatively moving a sample and said probe to a tunnel region and three-dimensionally driving said sample and said probe, said support means supporting said probe such that said probe is located between an objective lens of said optical microscope and said sample.

16. A scanning tunnel microscope according to claim 15, wherein said support means comprises means for supporting said probe in an objective lens of an optical microscope so as to locate said probe between said objective lens and said sample.

17. A scanning tunnel microscope according to claim 15, wherein said actuator means comprises a three-dimensional actuator comprising a piezoelectric element and arranged between said support means and said probe.

18. A scanning tunnel microscope comprising:
a probe arranged on an optical axis of an objective lens,
an actuator arranged on an outer frame of said objective lens,
fixing means for fixing said actuator on said objective lens,
optically-transparent probe-support means mounted at a distal end of said actuator for supporting said probe, and
an observation optical system arranged on an optical path of light reflected by said sample through an objective lens.

19. A scanning tunnel microscope, comprising:
a probe scanning mechanism consisting of an STM probe aligned with an optical axis of an objective lens of a sample observation optical system, a three-dimensional actuator for three-dimensionally driving said probe, and a probe moving mechanism for offsetting said probe from an optical axis of said sample observation optical system; and
an optical system adapted for observation of a sample surface,
wherein said mechanism for offsetting said STM probe from said optical axis of said objective lens is provided to cause said objective lens to come close a sample surface to allow an optical observation of an STM scanning area.

20. A scanning tunnel microscope according to claim 19, wherein said probe scanning mechanism comprises means for fixing said probe moving mechanism so as to fix a position of said probe with respect to said sample.

21. A scanning tunneling microscope comprising a fine movement element block having a probe and a fine movement element is disposed removably to a revolver of a microscope and a rough movement mechanism for moving a sample in the direction of said probe is disposed on a sample stage of said microscope.

22. A scanning tunneling microscope which is an apparatus for scanning tunneling microscopy by positioning a measurement position of a sample by optical observation means, said scanning tunneling microscope comprising at least one objective lens and an STM detection unit supported by a moving mechanism capable of positioning.

23. The scanning tunneling microscope according to claim 22, wherein said moving mechanism comprises a revolver unit capable of fixing a plurality of objective lenses.

24. A detecting and observing apparatus comprising:
a sample table for supporting a sample;
an optical microscope for observing the sample, the optical microscope having an optical path directed toward the sample;
a probe disposed within the optical path; and
an actuator for moving at least one of said probe and said sample table relative to each other.

25. An apparatus according to claim 24, wherein said probe is located in an optical field of said optical microscope.

26. An apparatus according to claim 25, wherein said probe detects a surface of the sample to form an image of the sample, and that part of the sample whose surface is detected by the probe is located in the optical field of said optical microscope.

27. An apparatus according to claim 26, wherein said optical microscope enables observation of both the sample and a position of the probe at the same time.

28. An apparatus according to claim 27, further comprising a detecting mechanism for detecting a distance between the sample and a tip of said probe.

29. An apparatus according to claim 28, wherein said detection mechanism has a concave lens, said probe and the sample are located at a focal point of the concave lens, and a distance between the probe and the sample is detected as a magnified erecting virtual image formed by the concave lens.

30. An apparatus according to claim 28, wherein said detecting mechanism comprises:
an optical fiber for applying illumination light to a gap between said probe and the sample in a line inclined relative to the optical axis of said optical microscope;
an auxiliary objective lens located to receive the illumination light reflected from the sample; and
an auxiliary ocular lens through which the illumination light detected by said auxiliary objective lens is observed.

31. An apparatus according to claim 24, wherein said optical microscope comprises a light source for emitting light and at least one objective lens disposed between the light source and the sample, and wherein said probe is disposed between said objective lens and the sample.

32. An apparatus according to claim 31, wherein said probe is adapted to be removably inserted into a space between said objective lens and the sample.

33. An apparatus according to claim 32, wherein said probe is disposed in substantially axial alignment with said objective lens while said probe is inserted between the sample and said objective lens.

34. An apparatus according to claim 31, wherein said objective lens has a central through hole, and said probe is supported to move through the central through hole of the objective lens.

35. An apparatus according to claim 31, wherein said objective lens is a convex lens.

36. An apparatus according to claim 31, wherein said optical microscope includes an ocular optical system, and said objective lens includes a reflection type objective lens which comprises a concave mirror for receiving light reflected from the sample and a convex mirror for guiding the light from the concave mirror to said ocular optical system, said concave mirror and said convex mirror being set in substantially axial alignment with said probe.

37. An apparatus according to claim 24, wherein said optical microscope has a plurality of objective lenses for enabling optical observation of the sample through a selected one of the objective lenses.

38. An apparatus according to claim 37, wherein said probe is integrated with one of said objective lenses, and said probe and the sample are observed through said selected one objective lens while said probe faces the sample.

39. An apparatus according to claim 24, further comprising a support member movably coupled to said probe such that the probe is adapted to be brought between the sample and the optical microscope.

40. An apparatus according to claim 39, further comprising a rotatable shaft having a rotating axis parallel with an optical axis of the optical microscope, and said support member is supported at one end by said rotatable shaft and being movably coupled to said probe at the other end.

41. An apparatus according to claim 37, further comprising a revolver having removably coupled thereto said probe and the objective lenses, such that at least one of said probe and one of said objective lenses opposes the sample.

42. An apparatus according to claim 41, wherein said probe is mounted to said revolver by means of said actuator.

43. An apparatus according to claim 24, further comprising an access unit for adjusting a distance between said probe and the sample.

44. An apparatus microscope according to claim 43, wherein said access unit adjusts the distance between said probe and the sample on the basis of a tunnel current flowing between said probe and the sample.

45. An apparatus according to claim 44, wherein said access unit adjusts the distance between said probe and the sample to maintain the tunnel current at a constant value.

46. An apparatus according to claim 24, wherein said actuator comprises a piezoelectric member and a plurality of electrodes provided on the piezoelectric member, and is designed to move said probe and said sample table relative to each other, in X-, Y- and Z-axis directions, when a voltage is applied to the piezoelectric member through the electrodes.

47. An apparatus according to claim 46, wherein said piezoelectric member is made of three piezoelectric elements for moving said probe and said sample table relative to each other, in the X-axis direction, Y-axis direction and Z-axis direction, respectively.

48. An apparatus according to claim 47, wherein said three piezoelectric elements are mounted one upon another in an axial direction of the probe.

49. An apparatus according to claim 47, wherein said three piezoelectric elements are rod-shaped members which intersect at right angles with one another, each of said members extending in the direction in which one of said probe and sample table is moved thereby.

50. An apparatus according to claim 46, wherein said piezoelectric member is shaped like a hollow cylinder, and said electrodes are provided to drive the piezoelectric member in the X-axis direction, Y-axis direction and Z-axis direction, respectively.

51. An apparatus according to claim 50, wherein said electrodes provided to drive said piezoelectric member in the X- and Y-axis directions include four elements provided on an outer circumferential surface of said piezoelectric member and spaced apart from one another, any adjacent two of which are designed to drive said piezoelectric member in different directions, and said electrode provided to drive said piezoelectric member in the Z-axis direction is ring-shaped and provided on the outer circumferential surface of said piezoelectric member.

52. An apparatus according to claim 51, wherein said electrodes include a hollow cylindrical rear electrode provided on an inner circumferential surface of said hollow cylindrical piezoelectric member and oppose said four electrodes and said ring-shaped electrode.

53. An apparatus according to claim 52, wherein said ring-shaped electrode is grounded.

54. An apparatus according to claim 50, wherein at least a part of said optical microscope is arranged in said hollow cylindrical piezoelectric member.

55. An apparatus according to claim 54, wherein said optical microscope comprises a light source for emitting light and an objective lens provided in said hollow cylindrical piezoelectric member, for applying to the sample the light emitted from the light source.

56. An apparatus according to claim 46, wherein said piezoelectric member is operatively coupled to the probe, and said piezoelectric member moves said probe in the X-, Y- and Z-axis directions.

57. An apparatus according to claim 46, wherein said actuator moves said sample table in the X- and Y-axis directions and said probe in the Z-axis direction.

58. An apparatus according to claim 46, wherein said actuator moves said probe in the X- and Y-axis directions and moves said sample table in the Z-axis direction.

59. An apparatus according to claim 24 wherein said actuator includes an XY-actuator operatively coupled to said probe, for scanning said probe, said probe and the XY-actuator constitute a scanning unit, and at least one of said optical microscope and scanning unit opposes the sample.

60. An apparatus according to claim 59, wherein said scanning unit is removable from the optical microscope.

61. An apparatus according to claim 60, wherein said probe is located in an optical field of said optical microscope while said scanning unit remains attached to the optical microscope.

62. An apparatus according to claim 61, wherein said scanning unit comprises a Z-actuator operatively coupled to said probe, for moving said probe in a direction perpendicular to X- and Y-axis directions so that said scanning unit moves said probe in X-, Y- and Z-axis directions.

63. An apparatus according to claim 59, further comprising a unit-moving mechanism for driving said scanning unit to move said probe between a first position where said probe opposes the sample and a second position which is different from the first position.

64. An apparatus according to claim 63, wherein said unit-moving mechanism has a support member spaced apart from the sample and supporting said scanning unit, the support member being movable so that the probe is brought between the sample and the optical microscope.

65. An apparatus according to claim 64, wherein said scanning unit comprises a Z-actuator for moving said probe in a direction perpendicular to X- and Y-axis directions, and said actuator comprises three piezoelectric elements for constituting said X, Y and Z actuators, said piezoelectric elements being rod-shaped ones which intersect at right angles with one another, each extending in the direction in which said probe is moved thereby.

66. An apparatus according to claim 64, wherein said optical microscope comprises an objective lens, and said unit-moving mechanism has a rotatable shaft having a rotating axis parallel with an optical axis of the objective lens, and said support member is connected at one end to said rotatable shaft and supports said scanning unit at the other end.

67. An apparatus according to claim 59, wherein said optical microscope allows observation of both said sample and a position of said probe at the same time.

68. An apparatus according to claim 67, wherein said optical microscope comprises an objective lens, and said probe is positioned in substantially axial alignment with an optical axis of said objective lens.

69. An apparatus according to claim 59, wherein said optical microscope includes a plurality of objective lenses and a revolver to which the objective lenses and said scanning unit are removably attached.

70. An apparatus according to claim 69, wherein said scanning unit is integrated with one of said objective lenses.

71. An apparatus according to claim 24, wherein said optical microscope includes:
   a light source for emitting light;
   an objective optical system for applying to the sample the light emitted from said light source and receiving the light reflected from the sample; and
   an ocular optical system through which an image of the sample formed from the light applied from said objective optical system is observed.

72. An apparatus according to claim 71, further comprising a detection optical system located in an optical path of the light reflected from the sample and then traveling through said objective optical system, for optically detecting the contour of a part of the sample.

73. An apparatus according to claim 71, wherein said probe is mechanically separated from said ocular optical system.

74. An apparatus according to claim 71, wherein said probe is mechanically separated from said objective optical system.

75. An apparatus according to claim 71, further comprising a video camera for receiving an image of a part of the sample through said objective optical system, and a video monitor for displaying the image of the part of the sample.

76. An apparatus according to claim 24, wherein said probe and the sample oppose each other in a closed space.

77. An apparatus according to claim 76, wherein said probe is mechanically separated from said optical microscope.

78. An apparatus according to claim 76, wherein said actuator is provided in the closed space, for moving said probe and the sample table relative to each other.

79. An apparatus according to claim 78, which further includes an optically transparent substrate supporting said probe, and in which said actuator moves the optically transparent substrate, thereby to move said probe in X-, Y- and Z-axis directions.

80. An apparatus according to claim 78, which further includes an optically transparent substrate supporting said probe, and in which said actuator moves the optically transparent substrate thereby to move said probe in X- and Y-axis directions, and moves said sample table in a Z-axis direction, respectively.

81. An apparatus according to claim 24, wherein said probe has a tip located in an optical field of said optical microscope.

82. An apparatus according to claim 24, wherein said probe has a tip, and the tip is spaced from the sample.

83. An apparatus according to claim 82, wherein the tip of the probe detects a tunnel current generated between the probe and the sample.

84. An apparatus according to claim 24, wherein the probe detects a surface of the sample to form an image of the sample, and the image of the sample is an image of a contour of the sample surface.

85. An apparatus according to claim 84, wherein the image of the contour of the sample surface is formed on the basis of a tunnel current generated between the probe and the sample.

86. A detecting and observing apparatus according to claim 84, wherein the image of the sample is obtained in atomic scale.

87. A detecting and observing apparatus according to claim 24, further comprising:
 a camera for receiving an optical image of the sample and outputting a sample observation signal on the basis of the optical image of the sample;
 a probe signal obtained by detecting the sample surface with the probe; and
 a memory storing the sample observation signal and the probe signal.

88. A scanning probe microscope according to claim 87, wherein said memory memorizes said sample observation signal and the probe signal as digital signals, respectively.

89. A method of detecting a sample surface by means of a microscope apparatus having a sample table for supporting a sample, an optical microscope for observing the sample, the optical microscope having an optical path directed toward the sample, a probe disposed within the optical path, and an actuator for moving at least one of said probe and said sample table relative to each other; said method comprising the acts of:
 observing the sample by means of said optical microscope; and
 detecting the sample surface by means of said probe.

90. A method according to claim 89, wherein said act of observing the sample includes an act of determining a particular part of the sample whose surface is to be detected by means of said probe.

91. A method according to claim 90, wherein said probe is disposed in an optical field of said optical microscope while said probe is detecting the sample surface.

92. A method according to claim 91, wherein the sample surface is detected on the basis of a tunnel current generated between said probe and that part of the sample whose surface is to be detected by means of said probe.

93. A method according to claim 90, wherein said act of detecting the sample surface includes an act of positioning said probe with respect to that part of the sample whose surface is to be detected by means of said probe.

94. A method according to claim 93, wherein said act of positioning said probe includes:
 an act of locating said probe above that part of the sample whose surface is to be detected by means of said probe; and
 an act of adjusting a distance between said probe and that part of the sample before said probe detects the surface of that part of the sample.

95. A method according to claim 94, wherein said act of adjusting the distance is to reduce the distance until a tunnel current is generated between said probe and that part of the sample.

96. A method according to claim 94, wherein said act of adjusting the distance includes:
 an act of relatively moving said probe and the sample close to each other until said probe and that part of the sample reach a determined positional relation; and
 reducing the distance until a tunnel current is generated between said probe and that part of the sample.

97. A method according to claim 89, wherein said act of detecting the sample surface includes:
 an act of moving at least one of said probe and the sample table relative to each other; and
 an act of forming an image of the sample by moving at least one of the sample and said probe relative to each other, so that the sample surface is detected by the probe.

98. A method according to claim 97, wherein an image of the sample is formed on the basis of a tunnel current generated between said probe and the sample.

99. A method for measuring a sample, using an optical microscope having an optical field and a probe being disposed within the optical field, comprising the acts of:
 optically observing the sample by the optical microscope while at least one of the sample and the optical microscope is moved relative to the other to search the sample for a particular part of the sample which is to be detected by the probe; and
 detecting the particular part of the sample, by means of the probe, while at least one of the sample and the probe is moved relative to the other.

100. A method according to claim 99, wherein said act of detecting includes:

an act of forming an image of the particular part of the sample.

101. A method according to claim 100, wherein the image of the particular part of the sample is formed on the basis of a tunnel current generated between the probe and the sample.

102. Detecting and observing apparatus comprising:

a sample table for supporting a sample;

an optical microscope for observing the sample, the optical microscope having an optical path directed toward the sample;

a probe disposed within the optical path; and an actuator operatively coupled to the probe.

103. A detecting and observing apparatus according to claim 102, wherein the actuator moves the probe in X-, Y- and Z-axis directions.

104. A detecting and observing apparatus according to claim 102, further comprising:

another actuator operatively coupled to the sample table;

wherein the actuator moves the probe in X- and Y-axis directions, and the other actuator moves the sample table in a Z-axis direction.

105. A detecting and observing apparatus according to claim 102, further comprising:

another actuator operatively coupled to the sample table;

wherein the actuator moves the probe in a Z-axis direction, and the other actuator moves the sample table in X- and Y-axis directions.

106. A detecting and observing apparatus according to claim 102, wherein the actuator comprises a piezoelectric member, and the piezoelectric member is shaped like a hollow cylinder.

107. A detecting and observing apparatus according to claim 102, wherein the actuator comprises three rod-shaped piezoelectric members extending in X-, Y- and Z-axis directions, respectively.

108. A detecting and observing apparatus according to claim 102, wherein the probe comprises a central axis;

wherein the optical path comprises a central optical axis; and wherein the central axis remains in substantial alignment with the central optical axis of the optical path.

109. A detecting and observing apparatus according to claim 102, wherein the optical microscope comprises a camera for receiving an optical image of the sample, and a monitor for displaying the optical image of the sample.

110. A detecting and observing apparatus according to claim 102, further comprising:

an optically measuring apparatus having a laser light source and integrated with the optical microscope.

111. A detecting and observing apparatus according to claim 102, wherein the probe comprises a tip, and the tip is apart from the sample surface.

112. A detecting and observing apparatus according to claim 102, wherein the probe detects a tunnel current generated between the probe and the sample surface, and the image of the surface is formed on the basis of the tunnel current.

113. A detecting and observing apparatus according to claim 102, wherein the optical microscope uses a reflected illumination.

114. A detecting and observing apparatus according to claim 102, wherein the optical microscope comprises at least one objective lens and a revolver, and the objective lens is removable from the revolver.

115. A detecting and observing apparatus according to claim 114, wherein the actuator is coupled to the revolver, and the actuator is removable from the revolver.

116. A detecting and observing apparatus according to claim 102, wherein said probe is located in an optical field of said optical microscope.

117. A detecting and observing apparatus according to claim 116, wherein a part of the sample whose surface is detected by the probe is located in the optical field of said optical microscope.

118. A detecting and observing apparatus according to claim 117, wherein the optical microscope enables observation of both the sample and a position of the probe at the same time.

119. A detecting and observing apparatus according to claim 102, wherein the probe detects a surface of the sample to form an image of the sample.

120. A detecting and observing apparatus according to claim 119, wherein the image of the sample is obtained in atomic scale.

121. A detecting and observing apparatus according to claim 102, wherein the actuator comprises a piezoelectric member.

122. A detecting and observing apparatus according to claim 121, wherein the actuator moves the probe in X-, Y- and Z-axis directions.

123. A detecting and observing apparatus according to claim 121, further comprising:

another actuator operatively coupled to the sample table, comprising a piezoelectric member;

wherein the actuator moves the probe in X- and Y-axis directions, and the other actuator moves the sample table in a Z-axis direction.

124. A detecting and observing apparatus according to claim 121, further comprising:

another actuator operatively coupled to the sample table, comprising a piezoelectric member;

wherein the actuator moves the probe in a Z-axis direction, and the other actuator moves the sample table in X- and Y-axis directions.

125. A scanning probe microscope comprising:

a sample table for supporting a sample;

an optical microscope for observing the sample, the optical microscope having an optical path directed toward the sample;

a probe disposed within the optical path; and an actuator for scanning at least one of said probe and said sample table relative to each other.

126. A scanning probe microscope according to claim 125, wherein the actuator is operatively coupled to at least one of the sample table and the probe.

127. A scanning probe microscope according to claim 126, wherein the actuator moves the probe in X-, Y- and Z-axis directions.

128. A scanning probe microscope according to claim 126, wherein the actuator moves the probe in X- and Y-axis directions, and the sample table in a Z-axis direction.

129. A scanning probe microscope according to claim 126, wherein the actuator moves the probe in a Z-direction, and the sample table in X-, Y-axis directions.

130. A scanning probe microscope according to claim 125, wherein the actuator comprises a piezoelectric member.

131. A scanning probe microscope according to claim 130, wherein the piezoelectric member is shaped like a hollow cylinder.

132. A scanning probe microscope according to claim 130, wherein the piezoelectric member is comprised of three piezoelectric elements, and the three piezoelectric elements are rod-shaped members extending in X-, Y- and Z-axis directions, respectively.

133. A scanning probe microscope according to claim 125, further comprising:
   another optical microscope for detecting a distance between the sample and a tip of the probe.

134. A scanning probe microscope according to claim 125, wherein each of the optical microscope and another optical microscope comprises an optical axis, and the optical axis of another optical microscope inclines to the optical axis of the optical microscope.

135. A scanning probe microscope according to claim 125, wherein the probe comprises a central axis; and
   the optical path comprises a central optical axis; and
   the central axis of the probe remains in substantially alignment with the central optical axis of the optical path.

136. A scanning probe microscope according to claim 125, wherein the optical microscope comprises a camera for receiving an optical image of the sample, and a monitor for displaying the optical image of the sample.

137. A scanning probe microscope according to claim 125, further comprising:
   an optically measuring apparatus having a laser light source, and integrated with the optical microscope.

138. A scanning probe microscope according to claim 125, wherein the probe comprises a tip, and the tip of the probe is part from the sample surface.

139. A scanning probe microscope according to claim 125, wherein the probe detects a tunnel current generated between the probe and the sample surface, and an image of the surface is formed on the basis of the tunnel current.

140. A scanning probe microscope according to claim 125, wherein the optical microscope uses the reflected illumination.

141. A detecting and observing apparatus according to claim 125, wherein said probe is located in an optical field of said optical microscope.

142. A detecting and observing apparatus according to claim 141, wherein a part of the sample whose surface is detected by the probe is located in the optical field of said optical microscope.

143. A detecting and observing apparatus according to claim 142, wherein the optical microscope enables observation of both the sample and a position of the probe at the same time.

144. A detecting and observing apparatus according to claim 125, wherein the probe detects a surface of the sample to form an image of the sample.

145. A detecting and observing apparatus according to claim 144, wherein the image of the sample is obtained in atomic scale.

146. A scanning probe microscope comprising:
   a sample table for supporting a sample;
   an optical microscope for observing the sample, the optical microscope having an optical field;
   a probe disposed within the optical field; and
   an actuator operatively coupled to the probe.

147. A scanning probe microscope according to claim 146, wherein the actuator moves the probe in X-, Y- and Z-axis directions.

148. A scanning probe microscope according to claim 146, further comprising:
   another actuator operatively coupled to the sample table;
   wherein the actuator moves the probe in X- and Y-axis directions, and the other actuator moves the sample table in a Z-axis direction.

149. A scanning probe microscope according to claim 146, further comprising:
   another actuator operatively coupled to the sample table;
   wherein the actuator moves the probe in a Z-axis direction, and the other actuator moves the sample table in X- and Y-axis directions.

150. A scanning probe microscope according to claim 146, wherein the actuator comprises a piezoelectric member.

151. A scanning probe microscope according to claim 150, wherein the piezoelectric member is shaped like a hollow cylinder.

152. A scanning probe microscope according to claim 150, wherein the piezoelectric member is made of three piezoelectric elements, and the three piezoelectric elements are rod-shaped members extending in X-, Y- and Z-axis directions, respectively.

153. A scanning probe microscope according to claim 146, further comprising:
   another optical microscope for detecting a distance between the sample and a tip of the probe.

154. A scanning probe microscope according to claim 153, wherein each of the optical microscope and the other optical microscope comprises an optical axis, and the optical axis of the other optical microscope is inclined relative to the optical axis of the optical microscope.

155. A scanning probe microscope according to claim 146, wherein the optical microscope comprises a camera for receiving an optical image of the sample, and a monitor for displaying the optical image of the sample.

156. A scanning probe microscope according to claim 146, further comprising: am optically measuring apparatus having a laser light source, and integrated with the optical microscope.

157. A scanning probe microscope according to claim 146, wherein the probe comprises a tip, and the tip of the probe is apart from the sample surface.

158. A scanning probe microscope according to claim 146, wherein the probe detects a tunnel current generated between the probe and the sample surface, and an image of the surface is formed on the basis of the tunnel current.

159. A scanning probe microscope according to claim 146, wherein the microscope uses the reflected illumination.

160. A scanning probe microscope according to claim 146, wherein the optical microscope allows observation of both the sample and a position of the probe at the same time.

161. A detecting and observing apparatus according to claim 146, wherein the probe detects a surface of the sample to form an image of the sample.

162. A detecting and observing apparatus according to claim 161, wherein the image of the sample is obtained in atomic scale.

163. A scanning probe microscope comprising:
   a sample table for supporting a sample;
   an optical microscope for observing the sample, the optical microscope having an optical field;
   a probe disposed within the optical field; and
   an actuator for scanning at least one of said probe and said sample table relative to the other.

164. A scanning probe microscope according to claim 163, wherein the actuator is operatively coupled to at least one of the sample table and the probe.

165. A scanning probe microscope according to claim 164, wherein the actuator moves the probe in X-, Y- and Z-axis directions.

166. A scanning probe microscope according to claim 164, wherein the actuator moves the probe in X- and Y-directions and the sample table in a Z-axis direction.

167. A scanning probe microscope according to claim 164, wherein the actuator moves the probe in a Z-axis direction, and the sample table in X- and y-axis directions.

168. A scanning probe microscope according to claim 163, wherein the actuator comprises a piezoelectric member.

169. A scanning probe microscope according to claim 168, wherein the piezoelectric member is shaped like a hollow cylinder.

170. A scanning probe microscope according to claim 168, wherein the piezoelectric member is made of three piezoelectric elements, and the three piezoelectric elements are rod-shaped members extending in X-, Y- and Z-axis directions, respectively.

171. A scanning probe microscope according to claim 163, further comprising:
another optical microscope for detecting a distance between the sample and a tip of the probe.

172. A scanning probe microscope according to claim 171, wherein each of the optical microscope and the other optical microscope comprises an optical axis, and the optical axis of the other optical microscope is inclined relative to the optical axis of the optical microscope.

173. A scanning probe microscope according to claim 163, wherein the optical microscope comprises a camera for receiving an optical image of the sample, and a monitor for displaying the optical image of the sample.

174. A scanning probe microscope according to claim 163, further comprising:
an optically measuring apparatus having a laser light source, and integrated with the optical microscope.

175. A scanning probe microscope according to claim 163, wherein the probe comprises a tip, and the tip of the probe is apart from the sample surface.

176. A scanning probe microscope according to claim 163, wherein the probe detects a tunnel current generated between the probe and the sample surface, and an image of the surface is formed on the basis of the tunnel current.

177. A scanning probe microscope according to claim 163, wherein the optical microscope uses a reflected illumination.

178. A scanning probe microscope according to claim 163, wherein the optical microscope allows observation of both the sample and a position of the probe at the same time.

179. A detecting and observing apparatus according to claim 163, wherein the probe detects a surface of the sample to form an image of the sample.

180. A detecting and observing apparatus according to claim 179, wherein the image of the sample is obtained in atomic scale.

181. A detecting and observing apparatus comprising:
a sample table for supporting a sample;
an optical microscope for observing the sample to locate an observation portion thereon, the optical microscope having at least one objective lens and an optical field;
a probe and an objective lens;
a support member having coupled thereto each of the probe and the objective lens, said probe being disposed apart from an axis of the objective lens by a predetermined distance;
an actuator for moving at least one of the sample table and the probe relative to each other, the actuator being coupled to at least one of the probe and the sample table;
wherein at least one of the sample table and the support member is mounted to movably shift relative to the other such that both the optical field of said optical microscope and the probe can oppose the observation portion of the sample, selectively one at a time.

182. A detecting and observing apparatus according to claim 181, wherein said actuator moves the probe in a Z-axis direction, and the sample table in X- and Y-axis directions.

183. A detecting and observing apparatus according to claim 181, wherein said actuator comprises a piezoelectric member.

184. A detecting and observing apparatus according to claim 181, wherein said support member comprises a revolver, the revolver has coupled thereto each of the probe and the objective lens, and the revolver rotatably shifts the objective lens and the probe such that either of the objective lens or the probe can selectively oppose the observation portion of the sample.

185. A detecting and observing apparatus according to claim 181, wherein the probe detects a surface of the sample to form an image of the sample.

186. A detecting and observing apparatus according to claim 185, wherein the image of the sample is obtained in atomic scale.

187. A detecting and observing apparatus comprising:
a sample table for supporting a sample;
a probe for detecting a surface of the sample to form an image of the sample;
an actuator for moving at least one of said probe and said sample table relative to each other;
an optical microscope for observing the sample; and
another optical microscope for detecting a distance between the sample and a tip of the probe.

188. A detecting and observing apparatus according to claim 187, wherein each of the optical microscope and another optical microscope comprises an optical axis, and the optical axis of another optical microscope inclines to the optical axis of the optical microscope.

189. A detecting and observing apparatus comprising:
means for supporting a sample;
means for observing the sample, said means for observing having an optical path directed toward the sample;
a probe disposed within the optical path; and
means for moving at least one of said probe and said means for supporting.

190. A detecting and observing apparatus according to claim 189, wherein said probe is located in an optical field of said means for observing.

191. A detecting and observing apparatus according to claim 190, wherein that part of the sample whose surface is detected by the probe is located in said optical field of said means for observing.

192. A detecting and observing apparatus according to claim 191, wherein said means for observing enables observation of both said sample and a position of said probe at the same time.

193. A detecting and observing apparatus according to claim 189, wherein said means for moving moves the probe in X-, Y-, and Z-axis directions.

194. A detecting and observing apparatus according to claim 189, wherein said means for moving moves said probe in X- and Y-axis directions, and said sample table in a Z-axis direction.

195. A detecting and observing apparatus according to claim 189, wherein said means for moving moves said probe in a Z-axis direction, and said sample table in X-, Y-axis directions.

196. A scanning probe microscope according to claim 189, further comprising:

means for detecting a distance between said sample and a tip of said probe.

197. A scanning probe microscope according to claim 196, wherein each of said means for observing and said means for detecting comprises an optical axis, and the optical axis of said means for detecting is inclined relative to the axis of said means for observing.

198. A scanning probe microscope according to claim 189, wherein said probe comprises a central axis, said optical path comprises a central optical axis, and said central axis of said probe remains in substantial alignment with said central optical axis of said optical path.

199. A scanning probe microscope according to claim 189, wherein said probe detects a tunnel current generated between said probe and said sample, and an image of the sample is formed on the basis of the tunnel current.

* * * * *